US005530100A

United States Patent [19]
Darling et al.

[11] Patent Number: 5,530,100
[45] Date of Patent: Jun. 25, 1996

[54] METHODS FOR PURIFICATION OF RECOMBINANTLY PRODUCED PROTEINS

[75] Inventors: Thomas L. J. Darling, Lafayette Hill; Lida Y. Akhnana, Audubon; Jonathan J. Mitschelen, Perkiomenville; Michael E. Hrinda, Gwynedd Valley, all of Pa.

[73] Assignee: Rhone-Poulenc Rorer Pharmaceuticals Inc., Collegeville, Pa.

[21] Appl. No.: 519,709

[22] Filed: May 7, 1990

[51] Int. Cl.[6] .............................. C07K 3/08; C07K 3/12; C07K 3/20; C07K 15/06

[52] U.S. Cl. .............................. 530/383; 435/69.6; 530/408; 530/410; 530/417; 530/422; 530/423; 530/424; 530/427

[58] Field of Search .............................. 530/383, 408, 530/410, 427, 415, 417, 422, 423, 424, 425; 435/69.6

[56] References Cited

U.S. PATENT DOCUMENTS

| | | | |
|---|---|---|---|
| 4,511,502 | 4/1985 | Builder et al. | 260/112 R |
| 4,511,503 | 4/1985 | Olson et al. | 260/112 R |
| 4,518,526 | 5/1985 | Olson | 260/112 R |
| 4,604,377 | 8/1986 | Fernandes et al. | 514/8 |
| 4,656,255 | 4/1987 | Seely | 530/412 |
| 4,673,641 | 6/1987 | George et al. | 435/68 |
| 4,734,362 | 3/1988 | Hung et al. | 435/68 |
| 4,748,234 | 5/1988 | Dorin et al. | 530/412 |
| 4,766,224 | 8/1988 | Rausch | 530/412 |
| 4,797,474 | 1/1989 | Patroni et al. | 530/351 |
| 4,816,440 | 3/1989 | Thomson | 514/12 |
| 4,828,989 | 5/1989 | Prior et al. | 435/68 |
| 5,043,429 | 8/1991 | Zimmerman et al. | 435/69.6 |
| 5,238,919 | 8/1993 | Zimmerman et al. | 514/8 |

OTHER PUBLICATIONS

Martson and Hartley, Methods in Enzymology, 1990, vol. 182, pp. 264–276.
Marston, Biochem. J. (1986) 240, pp. 1–12.
Babbitt, et al., Bio/Technology, 1990, vol. 8, pp. 945–949.
Frankel, et al., Proc. Natl. Acad. Sci. USA, 1991, vol 88, p. 1192.
Fish et al., Biochemical Society Transactions, 1988, vol. 16, p. 102.
Marston et al., Biochemical Society Transactions, 1988, vol. 16, p. 112.
Williams, et al., Science, vol. 215, pp. 687–689 (1982).
Beebee, Biochem. J. vol. 183, pp. 43–54 (1979).
Concino et al., J. Bacteriol., vol. 152 (1) pp. 441–450 (1982).
Gurney, Jr. et al., Anal. Biochem. vol. 139 pp. 25–34. (1984).
Armstrong et al., J. Bacteriol., vol. 161 (1) pp. 39–46 (1985).

*Primary Examiner*—Jeffrey E. Russel

[57] ABSTRACT

Recovery of the 52/48 kDa tryptic fragment of vWF or peptide subfragments thereof produced in the form of inclusion bodies from recombinant host cells is carried out by providing a washed recombinant host cell suspension, adding a detergent and subjecting the cells to mechanical disruption. A second detergent is added, followed by another mechanical disruption and centrifugation to a pellet. The pellet is resuspended in a buffer and subjected to another mechanical disruption. Inclusion bodies are washed, resuspended and then recovered. In addition, endotoxins and DNA are removed from inclusion bodies containing the 52/48 kDa tryptic fragment of vWF or peptide subfragments thereof by mechanically disrupting the inclusion bodies in an aqueous buffer containing a detergent. A washed pellet is formed from these mechanically disrupted inclusion bodies and dissolved in a denaturant. Alkylation is then performed and the suspension is subjected to column chromatography, where the alkylated fragment or subfragment is recovered by elution.

47 Claims, 13 Drawing Sheets

```
                                              27                                                    54
ATG GAT CCC TCA GGA AAG AAA GTC ACC TTG AAT CCC AGT GAC CCT GAG CAC TGC
 M   D   P   S   S   K   K   V   T   L   N   P   S   D   P   E   H   C 81                                                   108
CAG ATT TGC CAC TGT GAT GTT GTC AAC CTC ACC TGT GAA GCC TGC CAG GAG CCG
 Q   I   C   H   C   D   V   V   N   L   T   C   E   A   C   Q   E   P 135                                                   162
GGA GGC CTG GTG GTG CCT CCC ACA GAT GCC CCG GTG AGC CCC ACC ACT CTG TAT
 G   G   L   V   V   P   P   T   D   A   P   V   S   P   T   T   L   Y 189                                                   216
GTG GAG GAC ATC TCG GAA CCG CCG TTG CAC GAT TTC TAC TGC AGC AGG CTA CTG
 V   E   D   I   S   E   P   P   L   H   D   F   Y   C   S   R   L   L 243                                                   270
GAC CTG GTC TTC CTG CTG GAT GGC TCC TCC AGG CTG TCC GAG GCT GAG TTT GAA
 D   L   V   F   L   L   D   G   S   S   R   L   S   E   A   E   F   E 297                                                   324
GTG CTG AAG GCC TTT GTG GTG GAC ATG ATG GAG CGG CTG CGC ATC TCC CAG AAG
 V   L   K   A   F   V   V   D   M   M   E   R   L   R   I   S   Q   K 351                                                   378
TGG GTC CGC GTG GCC GTG GTG GAG TAC CAC GAC GGC TCC CAC GCC TAC ATC GGG
 W   V   R   V   A   V   V   E   Y   H   D   G   S   H   A   Y   I   G 405                                                   432
CTC AAG GAC CGG AAG CGA CCG TCA GAG CTG CGG CGC ATT GCC AGC CAG GTG AAG
 L   K   D   R   K   R   P   S   E   L   R   R   I   A   S   Q   V   K 459                                                   486
TAT GCG GGC AGC CAG GTG GCC TCC ACC AGC GAG GTC TTG AAA TAC ACA CTG TTC
 Y   A   G   S   Q   V   A   S   T   S   E   V   L   K   Y   T   L   F 513                                                   540
CAA ATC TTC AGC AAG ATC GAC CGC CCT GAA GCC TCC CGC ATC ACC CTG CTC CTG
 Q   I   F   S   K   I   D   R   P   E   A   S   R   I   T   L   L   L 567                                                   594
ATG GCC AGC CAG GAG CCC CAA CGG ATG TCC CGG AAC TTT GTC CGC TAC GTC CAG
 M   A   S   Q   E   P   Q   R   M   S   R   N   F   V   R   Y   V   Q 621                                                   648
GGC CTG AAG AAG AAG AAG GTC ATT GTG ATC CCG GTG GGC ATT GGG CCC CAT GCC
 G   L   K   K   K   K   V   I   V   I   P   V   G   I   G   P   H   A 675                                                   702
AAC CTC AAG CAG ATC CGC CTC ATC GAG AAG CAG GCC CCT GAG AAC AAG GCC TTC
 N   L   K   Q   I   R   L   I   E   K   Q   A   P   E   N   K   A   F 729                                                   756
GTG CTG AGC AGT GTG GAT GAG CTG GAG CAG CAA AGG GAC GAG ATC GTT AGC TAC
 V   L   S   S   V   D   E   L   E   Q   Q   R   D   E   I   V   S   Y 783                                                   810
CTC TGT GAC CTT GCC CCT GAA GCC CCT CCT CCT ACT CTG CCC CCC GAC ATG GCA
 L   C   D   L   A   P   E   A   P   P   P   T   L   P   P   D   M   A 837                                                   864
CAA GTC ACT GTG GGC CCG GGG CTC TTG GGG GTT TCG ACC CTG GGG CCC AAG AGG
 Q   V   T   V   G   P   G   L   L   G   V   S   T   L   G   P   K   R

891
AAC TCC ATG GTA TAA GTA GTT AAG CAT GC        FIG. 3
 N   S   M   V   *   V   V   K   H
```

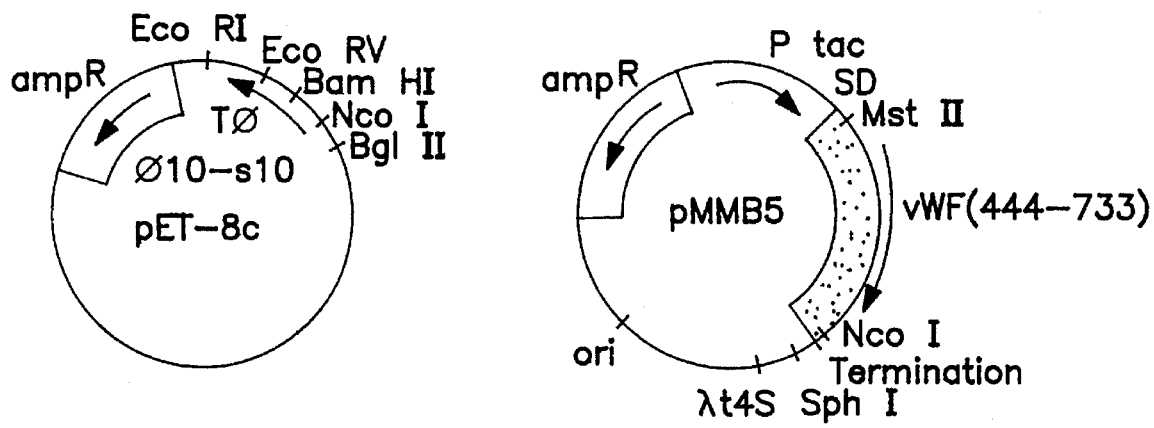
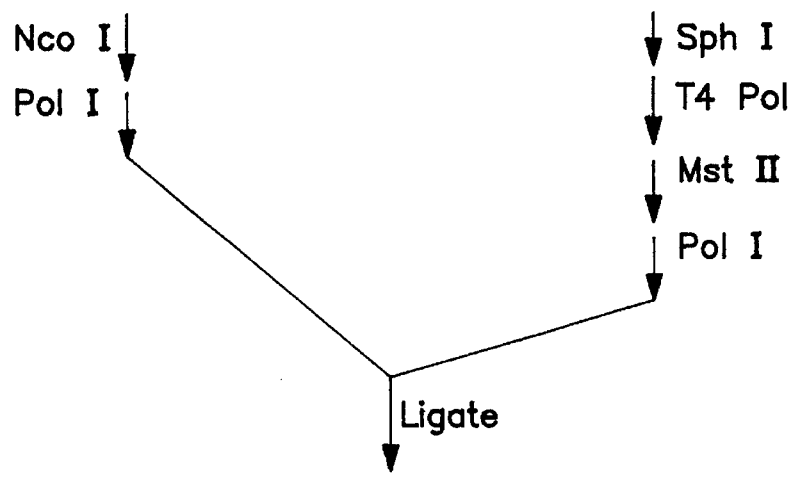
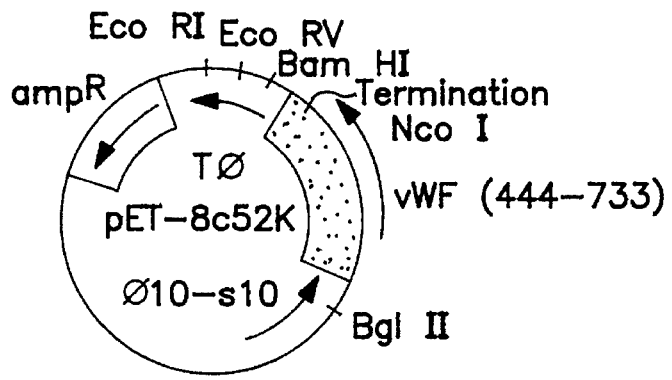
FIG. 5

METHODS FOR PURIFICATION OF RECOMBINANTLY PRODUCED PROTEINS

FIELD OF THE INVENTION

This invention relates generally to methods of purifying protein products from fermentation mixtures in which said products result from recombinant DNA-directed protein synthesis. More specifically, this invention relates to the recovery of von Willebrand Factor fragments from inclusion bodies present in a recombinant host cell.

The deposition of platelets at the site of vessel injury or malformation is thought to play an important role in thrombus formation in a number of thrombosis disease states including coronary artery occlusion and stroke. In addition, it may contribute to the occlusion of arterial grafts which can occur when either autologous vein segments or woven artificial graft prostheses are used. Platelet thrombus formation may also contribute to the thrombosis which can complicate attempts to relieve vessel obstruction by angioplasty.

Therefore, there is a need for a product which prevents platelet deposition at site of vessel injury, whether the injury occurs naturally or is induced as a result of iatropic manipulation such as those mentioned above. The peptides of the present invention have the ability to interfere with these undesired platelet depositions.

This invention relates inter alia to the purification of peptides which inhibit the binding of von Willebrand Factor (vWF) to platelets, heparin and collagen.

von Willebrand Factor (vWF) is a glycoprotein which is synthesized by endothelial cells and megakaryocytes and exists in plasma in multimeric forms. As a result of the initial isolation of vWF from the Factor VIIIC complex, vWF has also been variously referred to as the Factor VIII-related protein or more simply Factor VIII-R. vWF is known to play a central mediator role in the earliest stages of platelet deposition at the site of blood vessel wall injury. When the endothelial cell lining of a blood vessel is broken, vWF is required for the subsequent adhesion of platelets to the subendothelium. vWF functions by binding to one or more components of the subendothelium which may include collagen or the heparin-like glycosaminoglycans. vWF also binds to the platelet glycoprotein (GP) Ib receptor which causes platelets to adhere to the subendothelium. Binding of vWF to the GPIb receptor in turn triggers binding of fibrinogen to the platelet GPIIb/IIIa receptor and subsequent platelet aggregation.

The biosynthesis of vWF is a complex, multistep process involving extensive transcriptional and post-translational biochemical modifications, leading to the formation of high molecular weight glycosylated multimers of up to 20 MDa in size. As a consequence of this biosynthetic complexity, the opportunities for genetic defects to occur have presented themselves, manifesting in a number of disease states characterized by alterations in structure, function or vWF concentration. The term von Willebrand disease (vWD) defines this heterogeneous group of conditions of which several different subtypes are recognized.

Reported Developments

It is now appreciated that the production of recombinant proteins by genetically engineered host cells can result in the formation within the host cell of inclusion bodies, also referred to as refractile bodies. See for example D. C. Williams, et al., *Science* 215:687–89 (1982). Without wishing to be bound by any particular theory of inclusion body formation, it is believed that inclusion bodies arise, in part, from improper folding of the protein molecules resulting in insoluble aggregates within the host cell. Oligomerization of the proteins by means of intermolecular disulfide bonds or other mechanisms is also thought to contribute to inclusion body formation.

A number of protocols have been proposed to recover biologically active molecules from starting material comprising inclusion bodies. Many of the proposed methods involve an initial unfolding (i.e. denaturing) step where the inclusion body proteins are treated with a so-called chaotropic agent such as guanidine hydrochloride. At a subsequent stage in the protocol the denatured protein is renatured by removal of the chaotropic agent so as to assume its native conformation. See for example U.S. Pat. Nos. 4,511,502; 4,511,503; 4,518,526; and 4,604,377.

U.S. Pat. No. 4,656,255 discloses a method for recovering biologically active proteins from inclusion bodies. According to this invention improved yields result from the removal of reaggregated protein from process main streams, resolubilizing and reintroducing the protein to the main stream via a side stream compatible with the processes conditions of the main stream.

U.S. Pat. No. 4,673,641 relates to methods for stabilizing and purifying recombinantly produced proteins by co-producing aggregate forming proteins and recovering the protein of interest from the co-produced aggregate. According to one embodiment a nondenaturing aggregate purification protocol is disclosed wherein a cell suspension is treated with lysozyme, a non-ionic detergent (Nonidet P40, NP-40, Shell Trademark, polyoxyethylene (9) p-tert-octylphenol) is added and subject to cell disruption in a Polytron grinder (Brinkman Instruments). After centrifugation the pellet is resuspended in Triton X-100, a second polyoxyethylene (9-10) p-tert-octylphenol non-ionic detergent and reground with the Polytron grinder. This step may be repeated.

According to the so-called denaturing aggregation purification procedure the pellet of aggregate is further treated by addition of a denaturant such as 6M guanidine hydrochloride. Sonication or homogenization may be employed to resuspend the pellet in the denaturing agent.

U.S. Pat. No. 4,734,362 discloses a protocol for the purification of recombinant proteins characterized by the steps of disrupting host cells containing inclusion bodies by chemical and/or enzymatic means, solubilizing the protein, acid acylating free amino groups, optionally reversibly or irreversibly derivatizing sulfhydryl groups, separating the recombinant protein in N-acylated form and recovering same.

U.S. Pat. No. 4,748,234 provides a method for recovering inclusion bodies having the steps of disrupting the cells by homogenization or sonication, removing greater then 99% by weight of salts by diafiltration against distilled water, optionally adding 1-octanol to the desalted disruptate and redisrupting, increasing the density or viscosity of the second disruptate and subjecting same to centrifugation. The process may further comprise the steps of solubilizing the inclusion body material under reducing conditions, organically extracting the inclusion body material, recovering same, oxidizing and purifying the recovered product.

U.S. Pat. No. 4,766,244 discloses a method of purifying recombinantly produced protein from inclusion bodies comprising lysing host cells such as by homogenization, centrifuging to provide an inclusion body containing pellet, washing and resuspending in a urea, Triton X-100, dithioerythritol buffer, extracting in an ethanolamine-SDS solution, dialyzing away the SDS and adding urea to 6M and chromatographically purifying the protein product on an ionic-exchange resin.

U.S. Pat. No. 4,797,474 suggests the substitution of cationic surfactants for guanidine hydrochloride or urea as solubilizing agents for recombinant protein recovery from inclusion bodies.

U.S. Pat. No. 4,816,440 discloses a process for recovering β-human interferon or IL-2 including the steps of mechanically homogenizing host bacteria, separating cellular material by centrifugation, solubilizing the protein in SDS, extracting into 2-butanol and subsequently purifying the protein product.

U.S. Pat. No. 4,828,989 provides a method of purifying recombinantly human gamma interferon from inclusion bodies by breaking the host cell, extracting the protein by solubilizing with a chaotrope; renaturing the protein by rapid dilution of the denaturant and purification by covalent chromatography.

With respect to the structure, function and molecular genetics of vWF a substantial body of work has been reported.

Fujimura et al. in "von Willebrand Factor; A Reduced and Alkylated 52/48 kDa Fragment Beginning at Amino Acid Residue 449 Contains the Domain Interacting with Platelet Glycoprotein Ib", *J. Biol. Chem.* 261:381–385 (1986), partially characterized a vWF fragment but do not describe the carboxy-terminal sequence which is necessary to fully specify the fragment. Also in this paper, the property of direct binding of the fragment to the platelets was not demonstrated.

Fujimura et al. in "A 52/48 kDa Tryptic Fragment of von Willebrand Factor Which Begins With Amino Acid Residue 449 Binds to Platelet GPIb in the Absence of Ristocetin" (Abst.), *Blood* 66:334a (1985), do not fully specify the fragment nor the amino acid sequence responsible for the binding of the fragment to platelets.

Bockenstedt et al. in "Structural Basis of von Willebrand Factor Binding to Platelet Glycoprotein Ib and Collagen", *J. Clin. Invest.* 77:743–749 (1986) report that digestion of native vWF polymers with Staphylococcal V8 protease to yield a 285,000 Da fragment of unspecified structure and sequence that inter alia competes with $^{125}$I-vWF for binding to GPIb. This paper shows loss of activity once the fragment is alkylated and reduced.

Girma et al. in "Mapping of Distinct von Willebrand Factor Domains Interacting with GPIb and GPIIb/IIIa and with Collagen Using Monoclonal Antibodies", *Blood* 67(5): 1356–1366 (1986) report that a *S. aureus* V-8 protease digestion fragment, SpIII, representing the NH$_2$-terminal portion of vWF contains the binding domain for the platelet receptor GPIb. SpIII is heterogeneous on SDS-PAGE migrating as a 320 kDa homodimer of two 170 kDa chains and as a 280 kDa species composed of a 170 kDa chain and a 104 kDa polypeptide.

Houdijk et al. in "Identification of Functional Domain on von Willebrand Factor by Binding of Tryptic Fragments to Collagen and to Platelets in the Presence of Ristocetin", *Blood* 67(5):1498–1503 (1986) report the identification of a 116 kDa tryptic fragment of vWF which binds to the platelet GPIb receptor.

Sakariassen et al. in "Mediation of Platelet Adhesion to Fibrillar Collagen in Flowing Blood by a Proteolytic Fragment of Human von Willebrand Factor", *Blood* 67(5): 1515–1518 (1986) further characterized the SpIII V-8 protease fragment described above as containing a binding site for collagen in addition to the GPIb receptor binding domain.

Hondijk et al. in "Comparison of Tryptic Fragments of von Willebrand Factor Involved in Binding to Thrombin-activated Platelets with Fragments Involved in Ristocetin-induced Binding and Binding to Collagen", *Thrombosis and Haemostasis* 56(3):391–96 (1986), conclude that the ristocetin-binding domain (RBD), the collagen-binding domain (CBD), and the thrombin-binding domain (TBD) occur in separate regions of the vWF molecule and that the order from NH$_2$-terminal to COOH-terminal is RBD to CBD to TBD.

Fujimura et al. in "A Heparin-binding Domain of Human von Willebrand Factor", *J. Biol. Chem.* 262(4):1734–39 (1987), report that the platelet GPIb-binding domain of vWF resides in a 52/48 kDa tryptic fragment beginning with amino acid residue Val-449 and ending with amino acid residue Lys-728. Further a high affinity heparin binding site was also identified within the region. The two domains are thought to be in close proximity to one another but not to be precisely congruent.

Ruggeri et al. in "von Willebrand Factor and von Willebrand Disease", *Blood* 70(4):895–904 (1987), review the structural/functional relationships of various vWF binding domains and their relationship to disease treatment protocols.

Lynch et al. in "Molecular Cloning of cDNA for Human von Willebrand Factor: Authentication by a New Method", *Cell* 41:49–56 (1985) report the identification of a 2.4 Kb partial cDNA clone of human vWF. The clone encodes a polypeptide corresponding to the COOH terminal portion of vWF and reacts immunologically with anti-human vWF antibodies.

Ginsberg et al. in "Human von Willebrand Factor (vWF): Isolation of Complementary DNA (cDNA) Clones and Chromosomal Localization", *Science* 228:1401–1406 (1985) report the identification of a series of overlapping clones which span approximately 8.2 Kb of vWF mRNA. Using the clones as probes, the vWF gene was localized to human chromosome 12 by in situ hybridization.

Sadler et al. in "Cloning and Characterization of Two cDNAs Coding for Human von Willebrand Factor", *Proc. Natl. Acad. Sci. U.S.A.* 82:6394–6398 (1985); describe a partial amino acid sequence of vWF based on two non-overlapping clones.

Shelton-Inloes et al. in "cDNA Sequences for Human von Willebrand Factor Reveal Five Types of Repeated Domains and Five Possible Protein Sequence Polymorphisms", *Biochemistry* 25:3164–3171 (1986) report the isolation of four cDNAs that span 6.5 Kb of vWF mRNA and completely specify the 2050 amino acids of the subunit of mature secreted vWF and 24 amino acids of a precursor peptide. Domain A consisting of 193–220 amino acids present in three tandem repeats between residues 497–1111 lies within a 50 kDa tryptic fragment of vWF that binds to GPIb of resting platelets.

Titani et al. in "Amino Acid Sequence of Human von Willebrand Factor", *Biochemistry* 25:3171–3148 (1986), report the complete amino acid sequence of human vWF and identify the platelet glycoprotein Ib binding domain as being localized between residues 449–728 of the vWF monomer.

Bonthron et al. in "Structure of Pre-pro-von Willebrand Factor and its Expression in Heterologous Cells", *Nature*

324:270–273 (1986), disclose the successful heterologous expression of a 2,813 amino acid pre-pro vWF protein.

Fretto, et al. in "Substructure of Human von Willebrand Factor", *J. Biol. Chem.* 261(33):15679–689 (1986), confirm the localization of the platelet binding domain in the $NH_2$-terminal half of the vWF molecule.

Collins et al. in "Molecular Cloning of the Human Gene for von Willebrand Factor and Identification of the Transcription Inhibition Site",*Proc. Natl. Acad. Sci. U.S.A.* 84:4393–97 (1987), report the isolation of a series of overlapping cosmid genomic clones containing the entire coding region of the human gene for von Willebrand Factor.

Titani et al. in "Amino Acid Sequence of the von Willebrand Factor-binding Domain of Platelet Membrane Glycoprotein Ib, *Proc. Natl. Acad. Sci. U.S.A.* 84:5610–5614 (1987) disclose the complete amino sequence in a 293 amino acid region of the α-chain of GPIb that mediates vWF binding.

Mohri et al. in "Structure of the vWF Domain Interacting with Glycoprotein Ib", *J. Biol. Chem.* 263(34):17901–17904 (1988), provide evidence that binding of GPIb to vWF involves two limited non-contiguous regions of vWF each approximately 15 amino acids long and separated by a linear sequence of some 200 amino acids.

Mohri et al. in "Isolation of the vWF Domain Interacting with Platelet Glycoprotein Ib, Heparin and Collagen and Characterization of Its Three Distinct Functional Sites", *J. Biol. Chem.* 264(29):17361–67 (1989), report further details of the structural relationship of three vWF binding domains, including that a dimer of the GPIb site is required for ristocetin-induced platelet aggregation.

SUMMARY OF THE INVENTION

This invention provides a process for extracting endotoxin and DNA from a protein inclusion body-containing pellet comprising forming a buffered aqueous suspension of said inclusion bodies, the improvement comprising mechanically disrupting said inclusion bodies.

This invention also provides a process for extracting endotoxin and DNA from protein inclusion bodies in a lysed recombinant host cell suspension containing same comprising:

(a) providing an inclusion body pellet;

(b) mechanically disrupting said pellet in a buffer to provide resuspended inclusion bodies;

(c) recovering the inclusion bodies after washing by centrifuging the resuspended inclusion bodies.

According to another aspect of this invention a process for recovery of a protein produced in the form of inclusion bodies from recombinant host cells is provided comprising the steps of:

(a) providing a concentrated, washed recombinant host cell suspension;

(b) adding a first detergent;

(c) subjecting the cells to a first mechanical disruption to provide a lysed cell suspension;

(d) adding a second detergent to the lysed cell suspension;

(e) subjecting the cells to a second mechanical disruption;

(f) centrifuging the suspension to provide an inclusion body containing pellet;

(g) resuspending the pellet in a buffer comprising said first and second detergents;

(h) subjecting the pellet to a third mechanical disruption;

(i) recovering the inclusion bodies after washing and centrifugation.

According to another aspect of this invention, a process is provided wherein washed, recovered inclusion bodies are further subjected to the steps of:

(j) dissolving the washed inclusion bodies protein in a denaturant;

(k) alkylating the protein;

(l) subjecting the alkylated protein to column chromatography;

(m) recovering the alkylated protein from the column by elution.

BRIEF DESCRIPTION OF THE DRAWINGS

FIG. 3 is the complete coding sequence for vWF fragment in pMMB3.

FIG. 5 is a diagrammatic illustration of the cloning strategy used to construct plasmid pET-8c52K, a plasmid useful in practicing the invention.

DETAILED DESCRIPTION OF THE INVENTION

Figure 1:
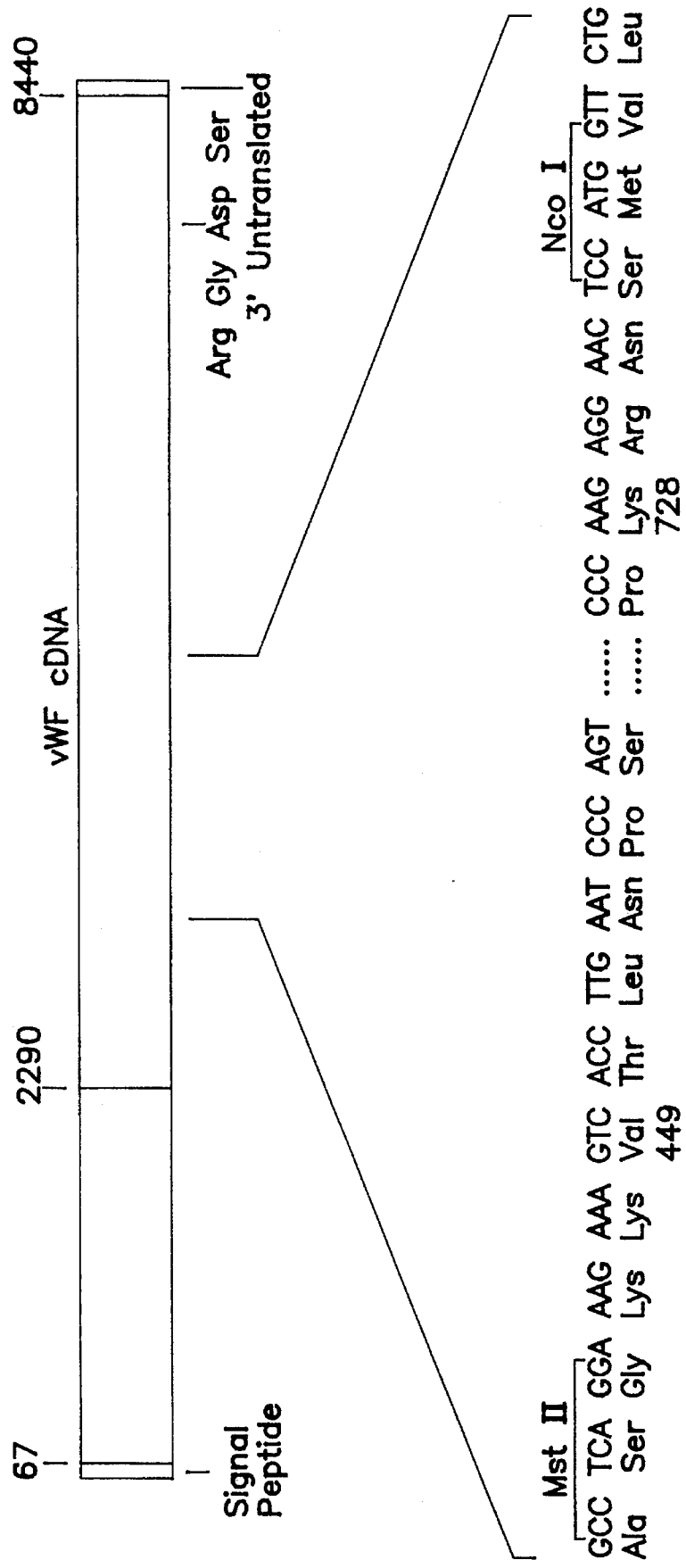
FIG. 1 is a diagrammatic illustration of the vWF gene. The location of the cDNA of the invention is indicated within the coding region of the mature vWF subunit.

As used herein the following terms have the following meanings:

Nucleotide—A monomeric unit of DNA or RNA consisting of a sugar moiety (pentose), a phosphate, and a nitrogenous heterocyclic base. The base is linked to the sugar moiety via the glycosidic carbon (1' carbon of the pentose) and the combination of base and sugar is called a nucleoside. The base characterizes the nucleoside. The four DNA bases are adenine ("A"), guanine ("G"), cytosine ("C"), and thymine ("T"). The four RNA bases are A, G, C and uracil ("U").

DNA Sequence—A linear array of nucleotides connected one to the other by phosphodiester bonds between the 3' and 5' carbons of adjacent pentoses. Heterologous DNA is DNA which can be introduced into a host organism from a source that does not normally exchange DNA with that host. e.g. human DNA used to transform *E. coli*.

Codon—A DNA sequence of three nucleotides (a triplet) which encodes through mRNA an amino acid, a translation start signal or a translation termination signal. For example, the DNA nucleotide triplets TTA, TTG, CTT, CTC, CTA and CTG encode the amino acid leucine ("Leu"), TAG, TAA and TGA are translation stop signals and ATG is a translation start signal.

Reading Frame—The grouping of codons during translation of mRNA into amino acid sequences. During translation the proper reading frame must be maintained. For example, the DNA sequence GCTGGTTGTAAG theoretically may be expressed in three reading frames or phases, each of which affords a different amino acid sequence:

GCT GGT TGT AAG-Ala-Gly-Cys-Lys

G CTG GTT GTA AG-Leu-Val-Val

GC TGG TTG TAA G-Trp-Leu-(STOP)

However, only one of the above reading frames encodes the correct genetic information. The translational start signal is recognized by the ribosome and accessory initiation factors to fix the correct reading frame.

Polypeptide—A linear array of amino acids connected one to the other by peptide bonds between the α-amino and carboxy groups of adjacent amino acids.

Genome—The entire DNA of a cell or a virus. It includes inter alia the structural genes coding for individual polypeptides as well as regulatory sequences such as operator, promoter and ribosome binding and interaction sequences, including sequences such as the Shine-Dalgarno sequences.

Structural Gene—A DNA sequence which encodes through its template or messenger RNA ("mRNA") a sequence of amino acids characteristic of a specific polypeptide. Structural genes may also have RNAs as their primary product such as transfer RNAs (tRNAs) or ribosomal RNAs (rRNAs).

Transcription—The process of producing RNA from a structural gene.

Translation—The process of producing a polypeptide from mRNA.

Expression—The process undergone by a structural gene to produce a product. In the case of a protein product it is a combination of transcription and translation.

Plasmid—A nonchromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. For example, a plasmid carrying the gene for tetracycline resistance ($Tet^R$) transforms a cell previously sensitive to tetracycline into one which is resistant to it. A cell transformed by a plasmid is called a "transformant".

Phage or Bacteriophage—Bacterial virus many of which consist of DNA sequences encapsulated in a protein envelope or coat ("capsid").

Cloning Vehicle—A plasmid, phage DNA or other DNA sequence which is able to replicate in a host cell, characterized by one or a small number of endonuclease recognition sites at which such DNA sequences may be cut in a determinable fashion for the insertion of heterologous DNA without attendant loss of an essential biological function of the DNA, e.g., replication, production of coat proteins or loss of expression control regions such as promoters or binding sites, and which contain a selectable gene marker suitable for use in the identification of transformed cells, e.g., tetracycline resistance or ampicillin resistance. A cloning vehicle is often called a vector.

Cloning—The process of obtaining a population of organisms or DNA sequences derived from one such organism or sequence by asexual reproduction or DNA replication.

Replicon—DNA required for replication in a particular organism, includes an origin of replication.

Recombinant DNA Molecule—A molecule consisting of segments of DNA from different genomes which have been joined end-to-end and have the capacity to infect some host cell and be maintained therein.

Expression Control Sequence—A sequence of nucleotides that controls and regulates expressing of structural genes when operatively linked to those genes. They include the lac system, major operator and promoter regions of phage lambda, the control region of fd coat protein and other sequences known to control the expression of genes of prokaryotic or eukaryotic cells and their viruses.

Mutation—A heritable change in the genetic information of an organism.

Mutant—An organism harboring a mutation. Generally expressing a discernible phenotype when compared to a standard reference strain of the species to which the organism belongs or to a wild-type population of that organism.

Peptide Sub-fragment—Any portion of a peptide fragment which retains biological activity. For example the vWF fragment of this invention is a peptide comprising about 280 amino acids. The bioactive peptides of 15–20 amino acids constitute sub-fragments of this larger peptide. The sub-fragment may be of any length from 15–20 amino acids up to but not including the full-length 280 amino acid fragment.

As indicated, the present invention relates to the purification of a polypeptide fragment which inhibits binding of vWF to platelets, heparin and collagen. This particular fragment was initially isolated as tryptic fragment of vWF that migrates in SDS-polyacrylamide gel electrophoresis (SDS-PAGE), under reducing conditions, as a 52/48 kDa doublet. The amino-terminal sequence, Val Thr Leu Asn Pro Ser Asp Pro Glu His Cys Gln, was found to be identical for both members of the doublet. This amino-terminal sequence was published in Fujimura et al., *J. Biol. Chem.* 261:381–385 (1986) supra. The published amino-terminal sequence was further proof that the molecular weight difference between doublet constituents was because of carbohydrate composition and established the position of this peptide within the intact vWF polypeptide of approximately 2050 amino acid residues as beginning with residue designated 449.

The characterization of the 52/48 kDa fragment by both its amino and carboxy-termini makes possible the identification of the nucleotide sequence that is essential for the expression of the fragment by recombinant DNA techniques. Through the use of such techniques the fragment is produced by bacteria, yeast, or other cells into which the nucleotide sequence for producing the fragment is inserted by techniques known to those of ordinary skill in the art. The identification of only the amino-terminal sequence of the 52/48 kDa fragment in Fujimura et al., *J. Biol. Chem.* 261:381–385 (1986) supra, makes it impossible for one of ordinary skill in the art to express the 52/48 kDa fragment since only by knowing the amino and carboxy-termini of a peptide fragment can the nucleotide sequence that encodes for this fragment be defined.

The carboxy-terminal sequence that is required along with the amino-terminal sequence for recombinant DNA expression of the 52/48 kDa fragment was determined in the following manner. A 55 kDa fragment of vWF which was produced by the same tryptic digestion that produced the 52/48 kDa fragment was found to have Asn Ser Met Val Leu Asp Val Ala Phe Val Leu Glu as an amino-terminal sequence. This amino-terminal sequence of the 55 kDa fragment was found to be carboxy-terminal to the 52/48 kDa fragment which had already had its amino-terminal sequence determined. Given this information it can be determined that the carboxy-terminus of the 52/48 kDa fragment ends just prior to the amino-terminal sequence of the 55 kDa fragment. Based on the knowledge of the amino-terminal sequence of the 55 kDa fragment and the known published partial amino acid sequence of vWF in Sadler et al., *Proc. Natl. Acad. Sci. U.S.A.* 82:6394–6398 (1985) supra, the amino acid sequence of the carboxy-terminal region of the 52/48 kDa fragment was determined. This carboxy-terminal region was determined to extend no further than the amino acid residue designated 729 in the intact vWF polypeptide. For an explanation of the basis for the numbering of the amino acids comprising the intact vWF polypeptide which was used for characterizing the 52/48 kDa fragment, see Fujimura et al., *J. Biol. Chem.* 61:381–385 (1986) supra.

With such information a nucleotide sequence can be inserted into the appropriate vector for expression of the 52/48 kDa fragment. For a description of recombinant DNA techniques for cloning vWF fragments, see Ginsburg et al., *Science* 228:1401–1406 (1985) supra and Sadler et al., *Proc. Natl. Acad. Sci. U.S.A.* 82:6394–6398 (1985) supra.

| One and Three-letter Amino Acid Abbreviations | | |
|---|---|---|
| A | Ala | Alanine |
| C | Cys | Cysteine |
| D | Asp | Aspartic Acid |
| E | Glu | Glutamic Acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |
| B | Asx | Asp or Asn, not distinguished |
| Z | Glx | Glu or Gln, not distinguished |
| X | X | Undetermined or atypical amino acid |

Genes coding for polypeptides such as Factor VIIIR or fragments of Factor VIIIR may be cloned by incorporating a DNA fragment coding for the polypeptide into a recombinant DNA vehicle (e.g., vector) and transforming suitable prokaryotic or eukaryotic hosts. Suitable prokaryotic hosts include but are not limited to Escherichia, Bacillus, Streptomyces and the like. Suitable eukaryotic hosts include but are not limited to yeast, such as Saccharomyces and cell cultures such as VERO, HeLa, mouse C127, Chinese hamster ovary (CHO), W138, BHK, COS-7 and MDCK. Such recombinant DNA techniques have now become well known and are described in *Methods in Enzymology*, (Academic Press), Volumes 65 and 68 (1979), 100 and 101 (1983), and the references cited therein. An extensive technical discussion embodying most commonly used recombinant DNA methodologies can be found in Maniatis, et al., *Molecular Cloning*, Cold Spring Harbor Laboratory (1982) or *Current Protocols in Molecular Biology*, Greene Publishing (1988).

One way of obtaining a DNA fragment encoding a desired polypeptide such as vWF is via cDNA cloning. In this process, messenger RNA (mRNA) is isolated from cells known or suspected of producing the desired protein. Through a series of enzymatic reactions, the mRNA population of the cells is copied into a complementary DNA (cDNA). The resulting cDNA is then inserted into cloning vehicles and subsequently used to transform a suitable prokaryotic or eukaryotic host. The resultant gene "library" is comprised of a population of transformed host cells, each of which contain a single gene or gene fragment. The entire library, therefore, provides a representative sample of the coding information present in the mRNA mixture used as a starting material.

Gene libraries can be screened using nucleic acid or antibody probes in order to identify specific DNA sequences. Once isolated, these DNA sequences can be modified or can be assembled into complete genes. Alternatively, as described in this invention, specific fragments of a gene can be engineered independently of the rest of the gene. Protein fragments encoded by these engineered gene fragments may not be found in nature, yet they may have significant utility in treating undesirable physiological conditions. The genetic engineering of vWF fragments for the prevention and/or the treatment of thrombosis is one such case.

Once the gene or gene fragment has been cloned, the DNA may be introduced into an expression vector and that construction used to transform an appropriate host cell. An expression vector is characterized as having expression control sequences as defined herein, such that when a DNA sequence of interest is operably linked thereto, the vector is capable of directing the production of the product encoded by the DNA of interest in a host cell containing the vector.

After the recombinant product is produced it is desirable to recover the product. If the product is excreted by the cell producing it, the product can be recovered from the fermentation medium. If the product is retained intracellularly, the cells must be physically disrupted such as by mechanical means, to release the intracellular product. Regardless of the method used to obtain the crude product be it either from the extracellular medium or as a result of extraction from an intracellular location, it is often desirable to purify the product.

In the case of a protein product, the purification protocol should not only provide a protein that is essentially free of other proteins but also free of other host cell contaminants. For example, when the host cell is a bacterium, such as *E. coli*, other host cell contaminants can include, but are not limited to, lipopolysaccharides such as endotoxin and nucleic acids such as DNA or RNA.

Accordingly, a useful recovery protocol should not only provide an essentially homogenous protein preparation in respect of any other coproduced recombinant protein or host proteins, but should also provide a recombinant protein product in which the level of non-protein contaminants are reduced to acceptable levels.

As mentioned above, a variety of host cells may be used for the production of the recombinant protein. The choice of a particular host organism is well within the purview of an ordinarily skilled artisan taking into account inter alia the nature of protein, its rate of synthesis, its rate of decay, and the characteristics of the recombinant vector directing the expression of the protein. Fermentation is carried out under conditions of sufficient time, temperature, and pH, to result in the formation of inclusion bodies comprising the recombinant protein within the host cells. The cells are harvested, washed and concentrated from the fermentation broth.

These procedures are conveniently performed using hollow fiber microfilter membrane cartridges. Other equivalents could of course be employed. For example, starting with 50 L of fermentation broth, two filter cartridges (Amicon H5MP01-43) in recirculating mode can be used to concentrate the cells to a volume of 2 to 4 liters, after which the cells are washed by diafiltration with 5 volumes (10–20) liters of Tris buffered saline. The cell concentration can range from about 0.01 to about 0.5 gm/ml, depending in part on the nature of the fermentation.

The concentrated, washed cell suspension is subjected to a first mechanical disruption. Any suitable cell disrupter may be employed, including but not limited to MANTON-GAULIN apparatus and French presses. A MICROFLUID-IZER (Microfluidics Corp, M-110Y) is conveniently employed. The cells may be disrupted directly in the Tris buffered saline or a first detergent may be added. If a detergent is employed a number of detergent types are useful. Detergents such as bile salts, cholate, deoxycholate, lithocholate may be used. Also useful are ionic detergents such as anionic, cationic or zwitterionic detergents. Guanidine salts, such as Guanidine hydrochloride and Guanidine thiocyanate may be used. However, when Guanidine salts are employed as detergents they are employed at concentrations of from about 1 mM to about 2M, with the upper limit being dictated by the point at which inclusion body protein begins to significantly dissolve in the salt. Dissolution of the inclusion body at this stage should be avoided. Polyoxyethylene sorbitol esters should be avoided as a first detergent. Deoxycholate is preferred as a first detergent and when present is preferably employed at a concentration of from about 0.001 to about 50 g/l, most preferably at about 0.5 g/l. After the first disruption one or more detergents are added to the lysed cell suspension. Any of the above-mentioned detergents may be used. Additionally, nonionic surfactants such as polyoxyethylene sorbitol ester or polyoxyethylene p-t octylphenol may be used. Specifically the Tween series, including Tween 20 and Tween 80, and Triton series, including Triton N-101 and NP-40, are preferred. Tween-80 or Triton X-100 are most preferred. When present Tween-80 is preferably used at a concentration of about 0.001% to about 50%, most preferably at about 0.025%.

After the second disruption, the inclusion bodies are pelleted by centrifugation. The pellet is washed extensively by repeated cycles of resuspension and centrifugation in a buffer. Normally, since the cells have been subjected to two cycles of disruption it is not necessary to repeat these steps and resuspension of the inclusion body pellet can be effected by routine homogenization. However, it has been surprisingly discovered that resuspension by means of passage through the cell disrupter can increase the efficiency of removal of non-protein contaminants. Accordingly, multiple cycles of washing in a buffer preferably containing at least two detergents wherein the washing is effected by resuspension and centrifugation have been shown to be quite effective in removal of endotoxin and DNA when the resuspension is carried by subjecting the essentially cell free pellet to disruption in a cell-disrupter such as the MICROFLUID-IZER. The maximum number of cycles is determined by efficiency of endotoxin removal balanced against mass loss due to repeated manipulation of the pellet; however, up to seven cycles have been effective. It is preferred that four cycles be performed. Optionally the final wash cycle can be accomplished in a buffer without the two detergents. Mechanical disruption of inclusion bodies as used herein means subjecting inclusion bodies to forces of such magnitude normally associated with cell disruption. Routine resuspension techniques such as by vortexing homogenization are not included by this definition.

The washed inclusion body protein is now ready for additional processing. For example, the inclusion body protein can be denatured, alkylated and subjected to column chromatography. Useful denaturants include chaotropic agents such as Guanidine salts or urea. NaCl or an equivalent salt can be optionally added to the chaotrope. When the denaturant is a Guanidine salt, Guanidine hydrochloride is preferred at a concentration from about 2.5M to about 8M. The preferred concentration being about 6M.

The alkylation is conducted in the presence of a sulfhydryl reducing agent such as dithiothreitol or β-mercaptoethanol by reaction with alkylating agents such as iodoacetamide or iodoacetate. After alkylation the protein is purified on Q-SEPHAROSE column chromatography. Essentially homogenous protein is eluted from the column by a 20–500 mM KCl salt gradient.

The following examples are given as illustrative of the present invention. The present invention is not restricted only to these examples and is applicable to any recombinantly produced protein such as blood proteins, antibodies, clotting factors and the like as well as growth factors such as fibroblast, epidermal and endothelial cell growth factors, that is recoverable in the form of inclusion bodies. It is also to be understood that reference herein to protein generally or to specific proteins such as von Willebrand Factor is not intended to be restricted to molecules which contain the full amino acid sequence of the natural protein. Rather is also intended to include fragments of the protein having various portions of the sequence deleted and protein or fragments thereof having various substitutions to or modifications of their natural sequences which do not destroy the biological activity associated with the protein or fragment.

EXAMPLE I

Expression of the 52 kDa vWF fragment

FIG. 1 indicates a diagrammatic representation of full-length vWF cDNA based on the nucleotide sequence described in Sadler et al. *Proc. Natl. Acad. Sci. U.S.A.* 82:6349 (1985) supra, and Shelton-Inloes et al. *Biochemistry,* 25:3164 (1986) supra. The 52 kDa tryptic fragment of vWF that binds to the platelet GPIb receptor is encoded by the central portion of the cDNA from amino acid residue 449 to residue 728 described by Titani et al. *Biochemistry,* 25:3171 (1986) supra. A cDNA clone encoding this region was provided by Dr. Dennis Lynch of Dana Farber Cancer Institute. The clone was originally isolated from a human umbilical vein endothelial cell cDNA library, and contained a 4 kb insert cloned via EcoRI linkers into the EcoRI site of pBR322. An EcoRI/SacI fragment from this clone was subcloned into GEMII to yield the vector pMMB1 (See FIG. 2). Nucleotide sequence analysis of pMMB1 indicated that an 857 bp MstII-NcoI fragment encodes the region of interest and contains only a few extra amino acid residues at both the amino and carboxy terminus when compared to the 52/48 fragment. (See FIG. 1)

Three vectors were used to demonstrate vWF fragment expression in *E. coli*. Vector pMMB3 used the highly efficient $P_R$ promoter from bacteriophage lambda. Induction of vWF fragment expression in *E. coli* can be achieved by growing the cells to mid-log phase at 30° C. and then shifting the temperature to 42° C. The second vector (pMMB5) used the hybrid trp-lac (tac) promoter system that is regulated by the lac repressor. Induction in this system is achieved by growing cells to mid-log phase at 37° C. followed by the addition of the lactose analog IPTG. The results obtained with pMMB3 and pMMB5 were very similar. Briefly, *E. coli* cells transformed with each of the above plasmids were grown to mid-log phase, induced for 1–16 hours, harvested, and fractionated into soluble and insoluble components. In both constructs the vWF fragment was produced at approximately 0.5% of total cell protein, and showed a similar time course of induction. Additionally, the vWF fragment exhibited extreme insolubility following lysis of either population of cells.

The third vector used for expression of the vWF fragment contained a promoter from the bacteriophage T7. In this system, the vWF DNA is placed into a vector containing the promoter and translation initiation signals for the Tφ protein of bacteriophage T7. T7 RNA polymerase can then be delivered to the host cell by either induction or infection. In the present example the vWF expression vector was placed into a cell that carries a prophage containing the gene for T7 RNA polymerase under control of the lac UV5 promoter. Addition of the lactose analog IPTG to a growing culture of cells induces T7 RNA polymerase, which in turn transcribes the target DNA in the plasmid. Transcription by T7 RNA polymerase is so active that target RNA can accumulate to amounts comparable to ribosomal RNA and target proteins can constitute the majority of cellular protein.

As an initial characterization of the synthesis of vWF fragment, cells were induced and samples taken at time points between 0.5 and 16 hours post induction. These data indicated that by 4 hours post induction, vWF fragment constituted approximately 25% of total cellular protein. This level was much higher than either the tac or $P_R$ vectors described above. For this reason, all subsequent work was performed with the T7 vector constructs.

Regardless of the vector system employed, the recombinant proteins were biologically active in that they inhibited botrocetin induced binding of intact $^{125}$I-vWF to platelets and also inhibited ristocetin-induced platelet aggregation in the presence of intact vWF.

A. Construction of the $P_R$ Expression Vector

The plasmid pDS19 was obtained from Dr. Dorothea Scandella, American Red Cross, Rockville, Md. This plasmid is a derivative of pCQV2 (Queen, *J. Mol. and Appl. Genet.*, 2:1 (1983)), and was used to provide a strong promoter, $P_R$ from bacteriophage lambda, a ribosome binding site, and an ATG translation initiation codon. The ATG codon overlapped a BamHI restriction site (GGATCC) as follows: ATGGATCC. pDS19 also contains the phage lambda cI857 temperature sensitive repressor which blocks transcription from $P_R$ at 30° C. but not at 42° C. Expression of a gene placed 3' to $P_R$ in this vector can thus be induced by shifting the temperature from 30° C. to 42° C.

Figure 2:
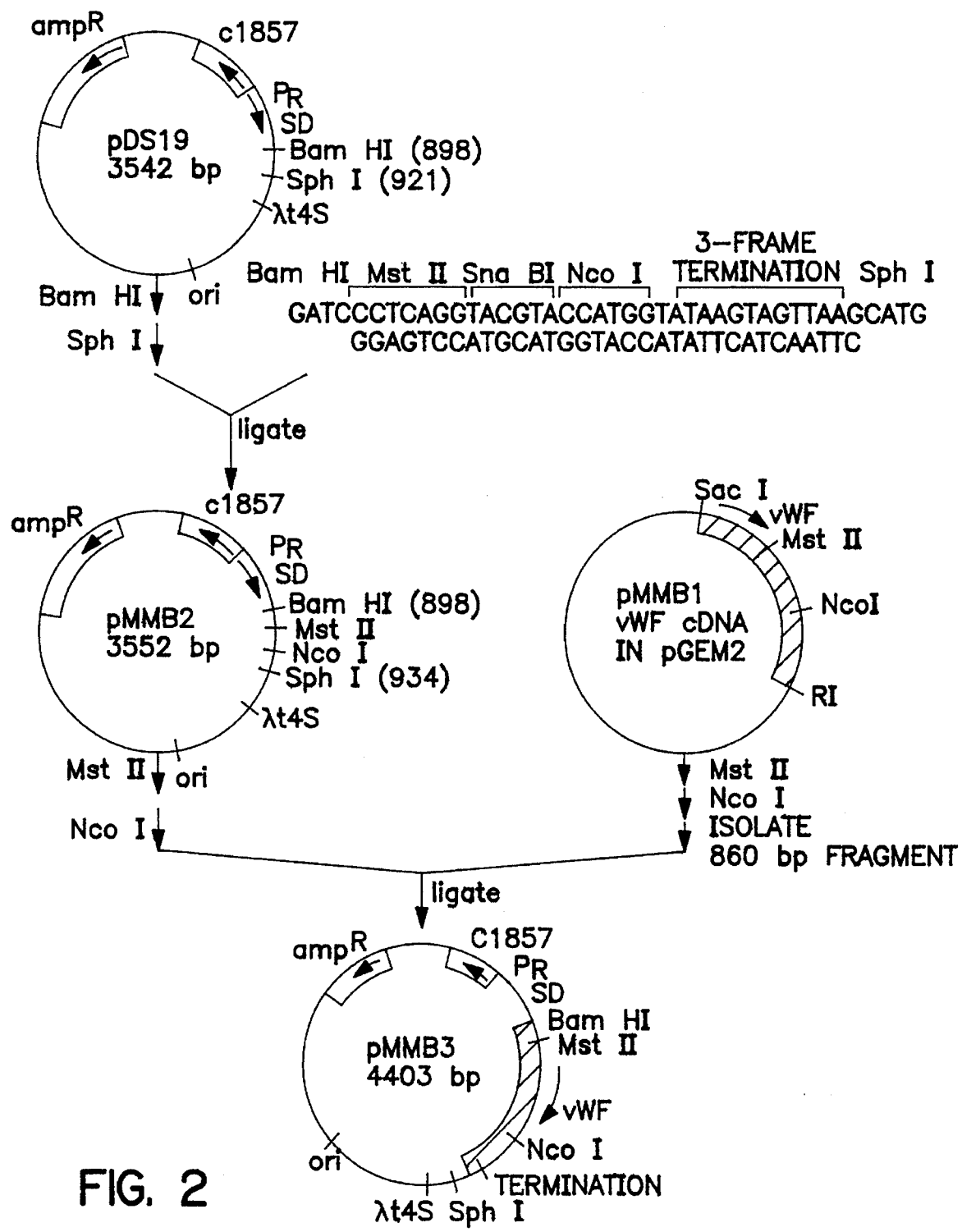
FIG. 2 is a diagrammatic illustration of the cloning strategy used to construct plasmid pMMB3, a plasmid useful in practicing the invention.

The strategy for cloning the DNA fragment encoding the 52,000 Da protein into pDS19 is shown in FIG. 2. All enzymes were used as suggested by the manufacturer.

pDS19 (10 µg) was digested with 20 U of BamHI and 10 U of SphI (Boehringer Mannheim) for 2 hours at 37° C. The DNA was then gel purified using Low Melting Point agarose (Bethesda Research Laboratories). The large fragment was excised and melted at 70° C., phenol extracted, and ethanol precipitated. Oligonucleotide linkers were added as shown in FIG. 2. The complementary oligonucleotides were annealed in 100 mM NaCl-10 mM Tris pH 7.8, 1 mM ETDA by heating at 65° C. for 10 minutes followed by slow cooling to room temperature. Twenty pmoles of the annealed oligonucleotides were ligated to 500 ng of pDS19 (BamHI, SphI) with 2.5 U T4 DNA ligase (Boehringer Mannheim) for 18 hours at 15° C. 5 ng of the ligation mixture was used to transform *E. coli* HB101 (BRL) and plated on LB agar and 100 µg/ml ampicillin at 30° C. The presence of the oligonucleotide linker was determined by restriction endonuclease analysis of plasmid DNA isolated from transformed colonies. Plasmid DNA from a single positive isolate was referred to as pMMB2 and was used for further constructions described below.

pMMB2 (10 µg) and a vWF cDNA clone designated pMMB1 (20 µg) were digested with MstII and NcoI (New England Biolabs) for 2 hours at 37° C. The large vector fragment and the 857 bp vWF fragment were gel purified as described below. The fragment (100 ng) was ligated to 400 ng of pMMB2 vector in the presence of 2.5 U T4 DNA ligase (Boehringer Mannheim) at 15° C. for 18 hours. As above, 5 ng of the ligation mixture was used for transformation. Plasmid DNA was isolated from individual transformants and the presence of the vWF insert was determined by restriction endonuclease cleavage analysis. A single positive isolate designated pMMB3 was used for expression of vWF fragment as described below (Section E). The complete nucleotide sequence of the coding portion of pMMB3 is indicated in FIG. 3.

B. Construction of the tac Expression Vector

Figure 4:
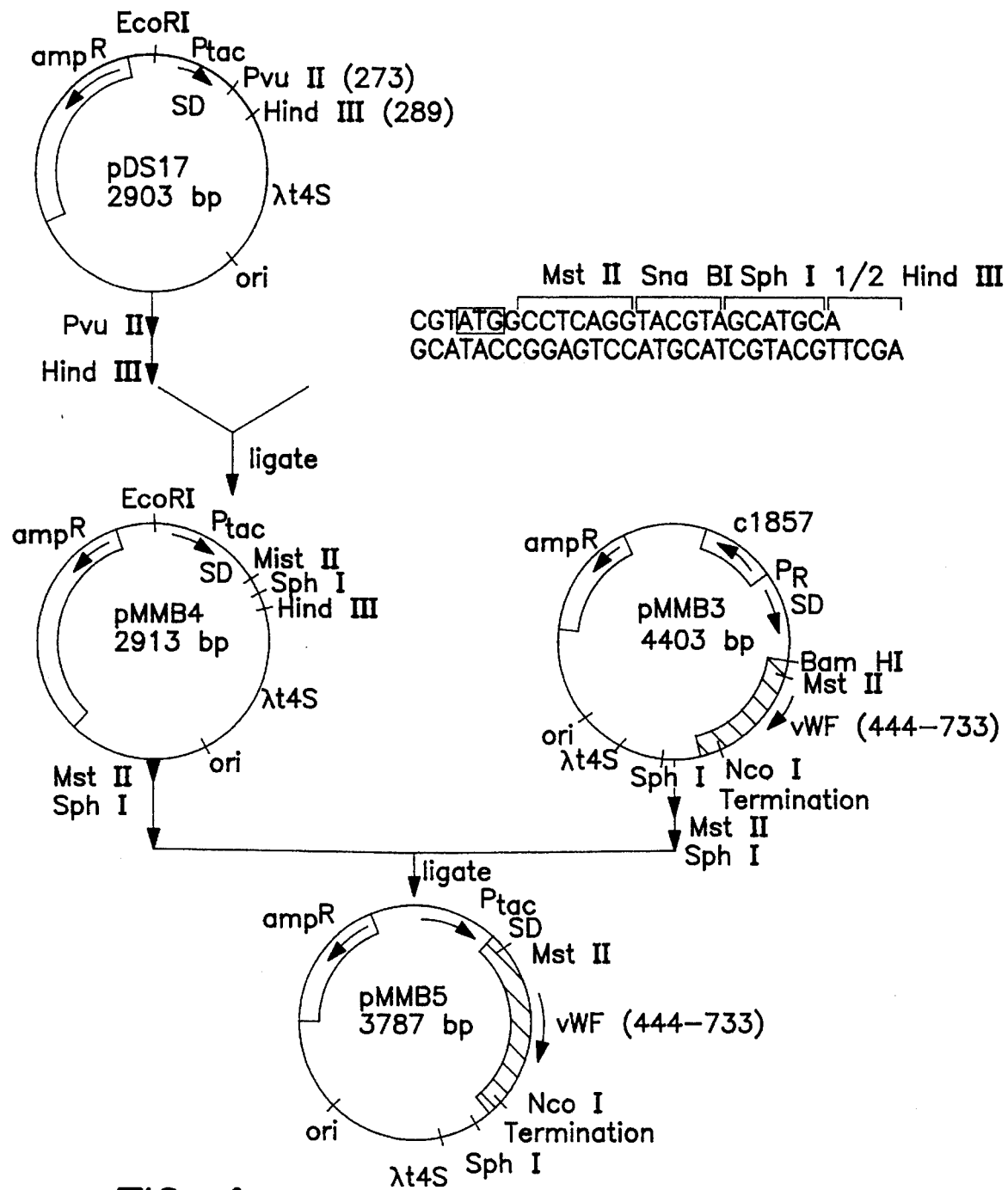
FIG. 4 is a diagrammatic illustration of the cloning strategy used to construct plasmid pMMB5, a plasmid useful in practicing the invention.

FIG. 4 is a diagrammatic representation of the construction of the tac vector for expression of the 52 kDa vWF fragment. The plasmid pDS17 was obtained from Dr. Dorothea Scandella, American Red Cross, Rockville, Md. This plasmid is a derivative of ptac12 (Amann et al. *Gene* 25:167 (1983)) and was used to provide a strong promoter, $P_{tac}$, a ribosome binding site, and a transcription terminator. Synthetic oligonucleotides were used to supply the ATG translation start signal as well as restriction enzyme sites to facilitate cloning of vWF cDNA.

pDS17 (10 μg) was digested with 20 U of PvuII and 20 U of HindIII (Boehringer Mannheim) for 2 hours at 37° C. The DNA was then gel purified using Low Melting Point agarose (Bethesda Research Laboratories). The large fragment was excised and melted at 70° C., phenol extracted, and ethanol precipitated. Oligonucleotide linkers were added as shown in FIG. 4. The complementary oligonucleotides were annealed in 100 mM NaCl-10 mM Tris pH 7.8, 1 mM EDTA by heating at 65° C. for 10 minutes followed by slow cooling to room temperature. Twenty pmoles of the annealed oligonucleotides were ligated to 500 ng of pDS17 (PvuII, HindIII) with 2.5 U T4 DNA ligase (Boehringer Mannheim) for 18 hours at 15° C. 5 ng of the ligation mixture was used to transform *E. coli* JM101 (BRL) and plated on LB agar and 100 μg/ml ampicillin at 37° C. The presence of the oligonucleotide linker was determined by restriction endonuclease analysis of plasmid DNA isolated from transformed colonies. Plasmid DNA from a single positive isolate was referred to as pMMB4 and was used for further constructions described below.

pMMB4 (10 μg) and the $P_R$ expression vector designated pMMB3 (20 μg) were digested with MstII and SphI (New England Biolabs) for 2 hours at 37° C. The large vector fragment and the 880 bp vWF fragment were gel purified as described above. The fragment (100 ng) was ligated to 400 ng of pMMB4 vector in the presence of 2.5 U T4 DNA ligase (Boehringer Mannheim) at 15° C. for 18 hours. As above, 5 ng of the ligation mixture was used for transformation of *E. coli* K12 JM101. Plasmid DNA was isolated from individual transformants and the presence of the vWF insert was determined by restriction endonuclease cleavage analysis. A single positive isolate designated pMMB5 was used for expression of vWF fragment as described below (Section F).

C. Construction of the T7 Expression Vector

FIG. 5 indicates a diagrammatic representation of the construction of the T7 vector for expression of the 2 kD vWF fragment. The plasmid pET-8c was obtained from Dr. F. William Studier of Brookhaven National Laboratories. This plasmid contains a fragment of T7 DNA specifying the gene 10 promoter inserted into the BamHI site of pBR322 so as to direct transcription counterclockwise. This plasmid also provides a transcription terminator for T7 RNA polymerase, a ribosome binding site and an ATG for translation initiation with the ATG overlapping an NcoI restriction site (CC ATGG).

The vector DNA (pET-8c) was digested with NcoI and the linear plasmid DNA was gel purified on Low Melting Point agarose as described above. Similarly, the insert containing plasmid (pMMB5) was digested with SphI and the 3' protruding termini made blunt ended by incubation with T4 DNA polymerase. Following cleavage with MstII the vWF fragment was gel purified as above.

The insert fragment (100 ng) and the vector (450 ng) were mixed and incubated in the presence of deoxyribonucleotides and the Klenow fragment of DNA polymerase I to fill-in protruding 5' termini. The vector DNA and the insert DNA were then ligated using T4 DNA ligase and the product used to transform *E. coli* DH-1. A clone containing the insert DNA in the correct orientation was identified and further confirmed by DNA sequence analysis.

To direct expression of the vWF gene, the recombinant plasmid was transferred into *E. coli* BL21 (DE3)pLysS, a lambda lysogen of BL21 (rB⁻mB⁻rif$_s$) in which the prophage carries a copy of the gene for T7 RNA polymerase under control of the lac UV5 promoter (Studier and Moffett, *J. Mol. Biol.* 189, 113–130 (1986)). This strain also contains a plasmid (pLysS) that directs expression of T7 lysozyme which serves to increase the tolerance of the host for maintaining toxic target plasmids (Studier et al., "Methods Enzymol." In Press)

Host BL21 (DE3) cells without the pLysS plasmid have also been used and express the 52/48 fragment at an equivalent level. These strains grow more slowly but appear to be more stable in storage when compared to the pLysS containing host. Downstream processing considerations not related to the invention as claimed herein may dictate the use of one or the other of these strains or a different host entirely.

D. Construction of the Kanamycin Resistant T7 Expression Vector

A plasmid (pET-8c(Km$^R$)) containing the T7 promoter and conferring resistance to kanamycin was obtained from Dr. F. William Studier of Brookhaven National Laboratories. The plasmid was constructed by removing the ampicillin resistance gene from pET-8c via excision of a BspHI-EcoRI fragment (pBR322 bp 3195–4361) and replacing it with an 869 bp fragment encoding kanamycin resistance (Km$^R$), with the Km$^R$ gene oriented clockwise in the vector. The Km$^R$ gene derives from Tn903 (Oka et al., *J. Mol. Biol.* 147:217–226 (1981)) and was obtained using the polymerase chain reaction with pUC4KISS (Barany F., *Gene* 37:111–123 (1985)) as template. The fragment carrying the Km$^R$ gene starts 50 nucleotides ahead of the Km$^R$ initiation codon and ends exactly at the termination codon.

A plasmid expressing the vWF fragment and conferring resistance to kanamycin was constructed from pET-8c52K (FIG. 5) and pET-8c(Km$^R$). Briefly, an XbaI/BamI fragment encoding the vWF fragment was excised from pET-8c 52K and ligated into XbaI/BamHI cleaved pET-8c(Km$^R$). The resulting plasmid DNA (pET-8c52K(Km$^R$)) was transformed into *E. coli* DH-1 cells and a single isolate was identified that released the appropriate size fragment by digestion with XbaI/BamHI. DNA from this isolate was then used to transform *E. coli* BL21 (DE3) pLysS. A single isolate from this transformation was then used for expression of vWF fragment as described below (Section F).

E. Expression of vWF Fragments in the $P_R$ Expression Vector

Plasmid DNA of pMMB3 was used to transform competent *E. coli* K12 HB101. Cultures of the transformed cells were grown in LB medium+50 μg/ml ampicillin at 30° C. until they reached $A_{595}$ of 0.4. They were shifted to 42° C. for 5 minutes and incubated further for a total of two hours at 40° C. The cells were pelleted by centrifugation and suspended in 0.1 volume sample buffer (Laemmli, *Nature*, 227:680 (1970)), and boiled 10 minutes.

F. Expression of vWF Fragments in the tac and T7 Expression Vectors

Overnight cultures of transformed cells were grown in LB media containing selective antibiotics. Cultures of T7 vector were selected in 100 μg/ml ampicillin or 30 μg/ml kanamycin in addition to 30 μg/ml chloramphenicol to select for pLysS. Cultures of the tac expression vectors were selected on ampicillin alone. Overnight cultures of transformed cells were diluted 1:100 and grown in LB medium at 37° C. until they reached $A_{595}$ of 0.4. Cultures were induced by adjusting to 0.5 mM IPTG and then incubated further for various times at 37° C. The cells were pelleted by centrifugation and suspended in 0.1 volume sample buffer (Laemmli, *Nature* 227:680 (1970)) and boiled 10 minutes.

G. Western Blot Analysis of vWF Fragments

Aliquots of approximately 50 μg protein from steps E and F above, were subjected to electrophoresis on 12% polyacrylamide-SDS gels (Laemmli, supra) and electroblotted onto nitrocellulose paper (Schleicher & Schuell, BA85). Procedures for electroblotting and reaction with antibodies were performed following procedures supplied by BioRad, Inc.

The primary antibodies used were either a rabbit polyclonal antibody specific for vWF or the RG46 monoclonal antibody, (Fujimura, et al., supra) specific for the 52 Kd tryptic fragment of vWF. The primary antibody was incubated with nitrocellulose paper for 15 hours at 23° C. The secondary antibody was either affinity purified biotinylated goat anti-rabbit or goat anti-mouse and was incubated for 30 minutes at 23° C. at a 1:10,000 dilution. After washing, the blot was treated with a streptavidin-biotin-horseradish-peroxidase conjugate as per manufacturers instructions (Vector Laboratories). A color development reagent obtained from Bio-Rad (4-chloro- 1-napthol) was used to visualize the vWF protein bands.

H. Platelet Aggregation

Platelet aggregation studies were carried out at a final platelet concentration of $1.6 \times 10^8$/ml in a Bio-data PAP-4 aggregometer with 0.2 ml of fixed washed platelets.

I. Characterization of pMMB3 and pMMB5 Expression

As mentioned above the results obtained with pMMB3 and pMMB5 were very similar. Briefly, E. coli cells transformed with each of the above plasmids were grown to mid-log phase, induced for 1–16 hour, harvested, and fractionated into soluble and insoluble components. In both constructs the vWF fragment was produced at approximately 0.5% of total cell protein, and showed a similar time course of induction.

Figure 6:
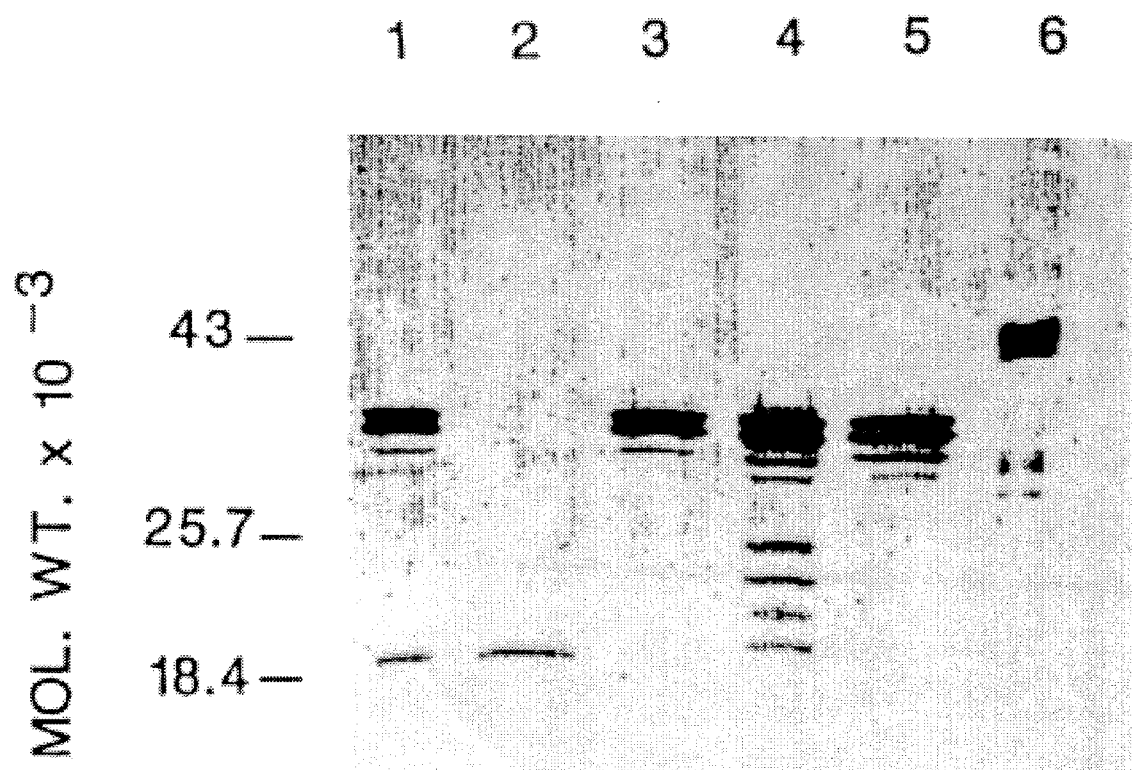
FIG. 6 is an illustration of a western blot depicting immunoreactive 33 kD vWF fragment at various steps in the initial purification from the bacterial lysate. The total amount of protein loaded per lane, in lanes 1–5 is 40 micrograms. Lane 6 contains 100 nanograms of the 52 kD tryptic fragment of native vWF. The western blot was reacted with a mouse monoclonal antibody to the 52 kD tryptic fragment of native vWF. Detection was achieved using a biotin labeled goat anti mouse IGG second antibody, and an avidin-biotin-horseradish peroxidase complex. Lane 1 is from total bacterial lysate. Lane 2 is supernatant from centrifuged bacterial lysate. Lane 3 is the pellet from centrifuged bacterial lysate. Lane 4 is the supernatant from a 2M urea wash and centrifugation of previous pellet. Lane 5 is the pellet from the 2M urea wash and centrifugation.

The vWF fragment exhibited extreme insolubility following lysis of either population of cells (FIG. 6, lanes 1–3). Additionally, washing the insoluble inclusion bodies with 2M urea resulted in approximately 5% of the total protein being released into the supernatant as well as substantial quantities of DNA.

Although, this supernatant contained some vWF fragment (FIG. 6, lane 4) the majority remained insoluble in 2M urea (FIG. 6, lane 5).

Figure 7:
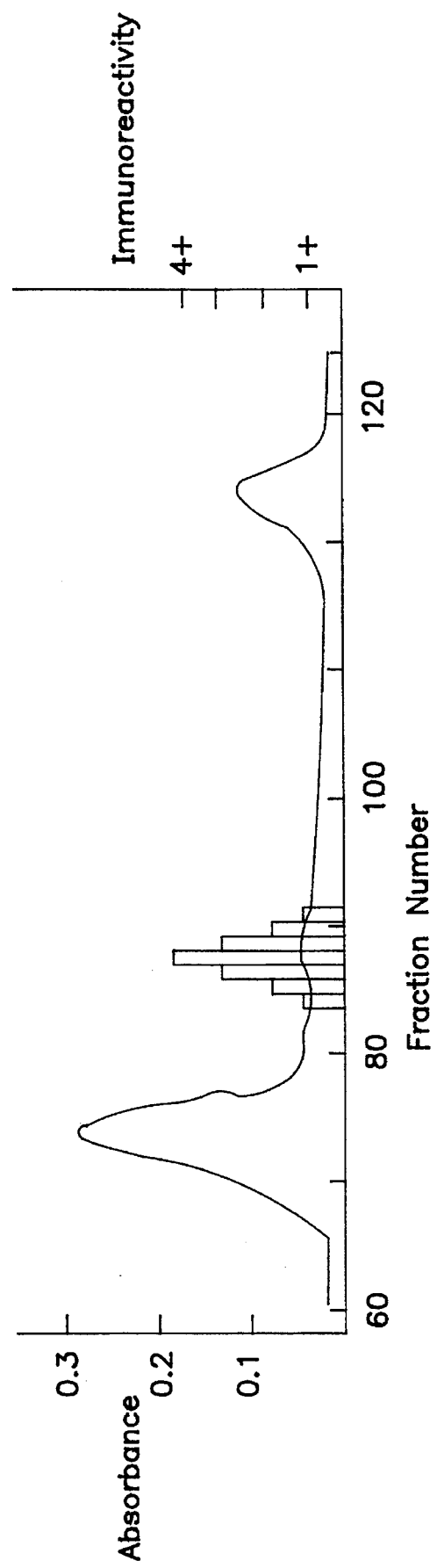
FIG. 7 is an illustration of a gel filtration elution profile of a crude *E. coli* lysate.

In order to obtain soluble material, the washed inclusion bodies were dissolved in 6M Guanidine hydrochloride, 10 mM DTT and then alkylated using iodoacetamide. The reduced and alkylated fragment was then subjected to gel filtration on Sephacryl S-200 equilibrated in 6M urea 0.1M acetic acid. A typical elution profile is shown in FIG. 7. Fractions containing immunoreactive vWF fragment were pooled, dialyzed and concentrated via ultrafiltration. SDS gel electrophoresis followed by staining with Coomasie blue indicated that the material was 50–75% pure at this stage of purification.

Figure 8:
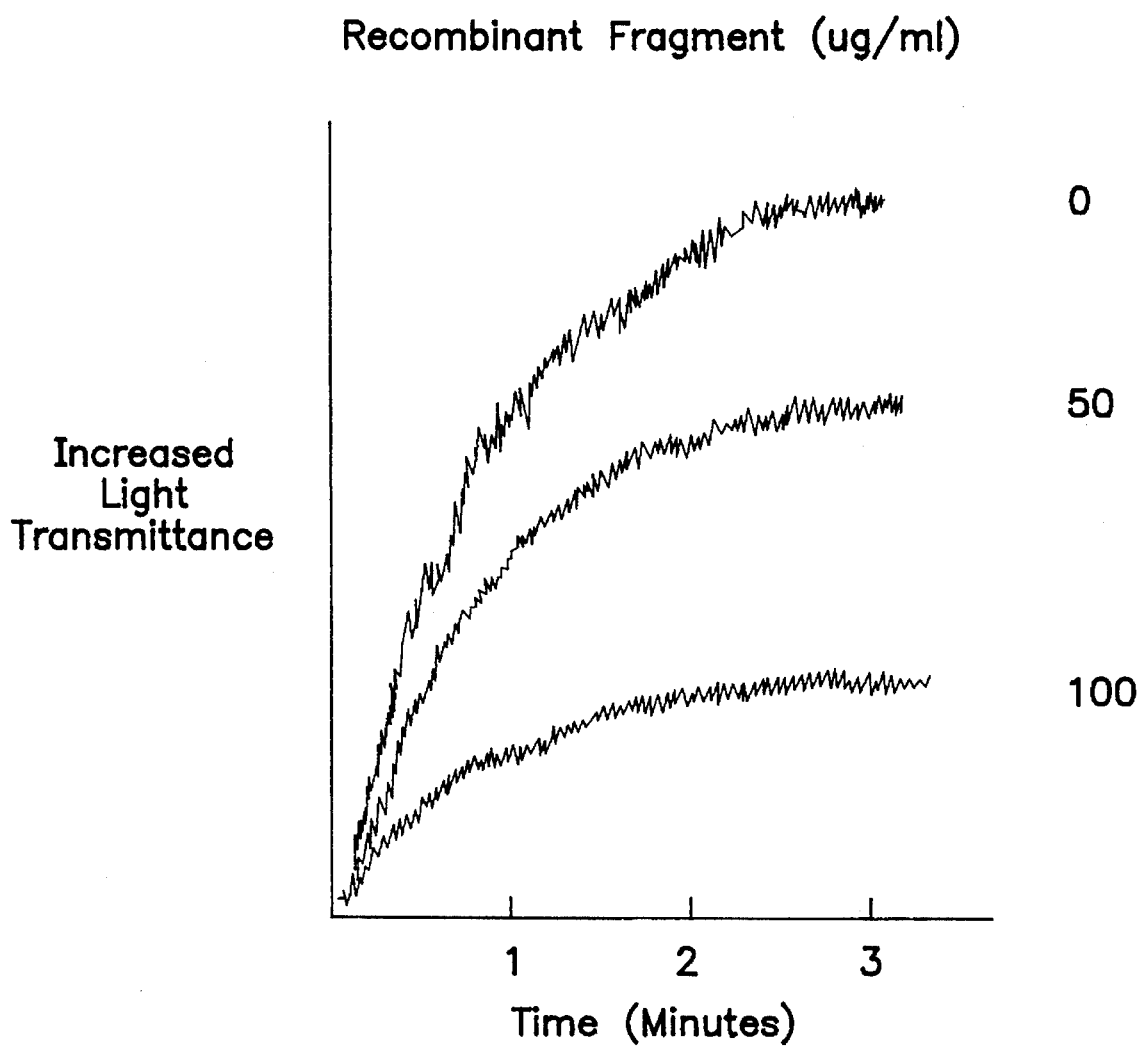
FIG. 8 is an illustration of the effect of a recombinant peptide of the invention on ristocetin-induced platelet aggregation.

The material purified by gel filtration was next examined for its ability to inhibit in vitro platelet aggregation. The data shown in FIG. 8 indicates that two different concentrations of the recombinant vWF fragment causes a dose-dependent reduction in ristocetin induced platelet aggregation. This reduction was similar to the reduction caused by the concentration of the non-recombinant vWF fragment (data not shown). Additionally, the same concentrations of a recombinant fragment of Factor VIIIC purified in an identical fashion failed to inhibit ristocetin-induced platelet aggregation (data not shown). Experiments indicate that the recombinant vWF fragment prepared from the T7 promoter constructs inhibited ristocetin-induced platelet aggregation in an identical fashion to the fragment purified from the $P_R$ promoter construct.

Figure 9:
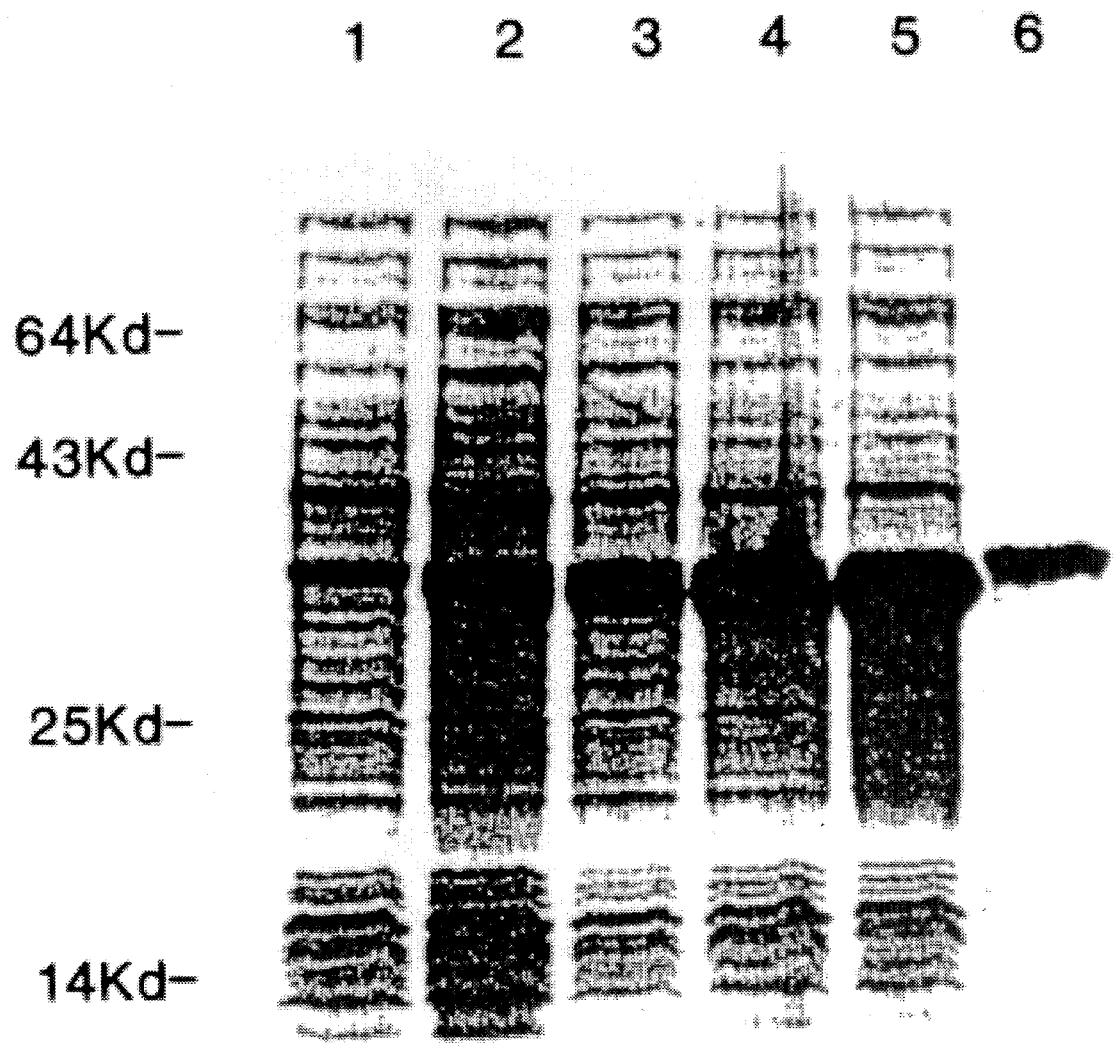
FIG. 9 is an illustration of a stained gel of the T7 expression product with an illustration of essentially homogeneous vWF fragment (lane 6).

J. Isolation and Characterization of vWF Produced by the Recombinant T7 Expression System In order to obtain sufficient material for biochemical characterization, cells were collected and used for protein purification. Lysis of the cells followed by a brief centrifugation yielded an insoluble fraction that was enriched for vWF fragment. Further purification of this fraction by solubilization in 6M Guanidine hydrochloride followed by reduction, alkylation and ion exchange chromatography on Q-SEPHAROSE yielded an essentially homogeneous fragment (FIG. 9, lane 6), that was soluble in physiological solutions and having an apparent molecular weight of about 33,000 Da. (+/−1,000). Accordingly, a seed culture was grown up overnight at 37° in medium containing chloramphenicol (25 mg/liter) and kanamycin (30 mg/liter). Fermentation was carried out at a scale of 50 liters, at 37° C., in an MPP 80 fermenter (manufactured by New Brunswick Scientific). Fermentation was carried out at pH 7, maintained by microprocessor controlled addition of either $NH_4OH$ or $H_3PO_4$ as needed. Foaming was maintained at pre-determined levels by the microprocessor controlled addition of antifoam (Mazu DF 204). The overnight seed culture (0.5 liter) was transferred to the fermenter which has been prepared with 50 liters of medium (Water for injection is used for medium preparation. NZY Broth (BBL, catalogue #99309) is dissolved at 21 grams/liter in warm water for injection. The dissolved medium is filtered through a glass fiber prefilter, then through a 0.22 micron filter. The filtration removes material which otherwise discolors the inclusion bodies.) The 50 liter batch of medium in the fermenter was prepared without antibiotics—the only antibiotics present are the residual chloramphenicol and kanamycin carried over in the 0.5 liter seed. The bacteria were grown with agitation (impeller at 200 RPM), and with aeration of 0.5 volumes of air per volume of liquid per minute. A typical time course of the growth and induction showed that the measured oxygen levels decrease as the cells grow. Induction was usually begun after approximately three hours growth, when cells have reached an $OD_{595\ nm}$=0.8–1.0 after which time the oxygen had declined to about 60% saturation.

Induction of expression was by addition of IPTG (isopropyl-beta-D-thiogalactopyranoside) to reach a final concentration of 0.4 mM. Induction with IPTG caused the culture to grow more slowly. Agitation was maintained at 200 RPM. It was routinely observed that the dissolved oxygen rises during the induction period. Induction proceeded for approximately three hours, after which fermentation was stopped.

Cells were harvested and concentrated using hollow fiber microfilter membrane cartridges. Two Amicon H5MPO143 filter cartridges were employed in a recirculating mode. Cells were concentrated to a volume of 2 to 4 liters on the Amicon filters, after which the cells were washed by diafiltration in the Amicon filtration apparatus with 5 volumes, approximately 10 to 20 liters, of Tris buffered saline (0.025M TRIS, 3.03 gms/liter $H_2O$, 0.2M NaCl, 11.7 gms/liter $H_2O$, Final pH 7.5±0.2, 25° C.; referred to hereinafter as A-1).

Cells were recovered from filtration in 4 liters of Tris buffered saline (A-1). In preparation for disrupting the cells, sodium deoxycholate was added to the cell suspension to reach a final concentration of 0.5 g/liter. The cells were mechanically disrupted by passage through a Microfluidizer® (Microfluidics Corp., M-110Y Microfluidizer®) immediately after collection. After the cells had passed once through the Microfluidizer®, a second detergent, Tween 80 was added to the suspension of lysed cells to reach a final concentration of 0.025%. (2.5% TWEEN 80 (v/v), 25 ml/liter TBS). Heat TBS Buffer A-1 and add Tween 80 dropwise into the solution and mix until it is visibly homogeneous. The solution is cooled to room temperature and then added to the disrupted cell suspension to yield a final concentration of 0.025% (v/v); hereinafter A-2). If the Tween is present in the first passage, the Microfluidizer® can become obstructed and will require clearing the flowpath before cells can be disrupted.

After the cells have been disrupted, the suspension was centrifuged (10,000×g; 35 minutes, 4° C.) to separate the inclusion bodies, which are primarily product, from the soluble cell debris. At this stage, the inclusion bodies may be stored overnight at −20° C.

The inclusion bodies were resuspended in 35 ml of Tris buffer A-3 per gram of inclusion body wet weight, determined by difference in weight of the centrifuge tube (A-3— 0.05M TRIS, 6.06 gms/liter $H_2O$, 1.21 mM sodium deoxycholate, 0.5 gms/liter $H_2O$, 2 mM dithiothreitol (DTT), 0.31 gms/liter $H_2O$, 2 mM EDTA, 0.74 gms/liter $H_2O$, 5% (v/v) glycerol, 50 ml/liter $H_2O$, 0.025% (v/v) TWEEN 80, 10 ml 2.5% TWEEN 80 (A-2)/liter $H_2O$, Final pH 9.0±0.2, 25° C.) The inclusion body pellets were routinely resuspended in buffer by using a Polytron homogenizer (Brinkmann). The resuspended inclusion bodies were passed through the Microfluidizer® to assure thorough mixing with the buffer. After passage through the Microfluidizer®, the inclusion bodies were collected by centrifugation. The wash procedure was carried out a total of three times with Tris buffer A-3. At the end of the third wash, the pelleted inclusion bodies are resuspended in Tris buffer A-4, which does not contain the detergents deoxycholate or Tween (A-4—0.05M TRIS, 6.06 gms/liter $H_2O$, 2 mM dithiothreitol (DTT), 0.31 gms/liter $H_2O$, 2 mM EDTA, 0.74 gms/liter $H_2O$, 5% (v/v) glycerol, 50 ml/liter $H_2O$, Final pH 9.0±0.2, 25° C.

The fourth and last wash was carried out with Tris buffer A-4. The crude product was collected after centrifugation, drained dry, and may be stored at −70° C. The overall mass yield is 70%. Pellets were redissolved in sufficient 6M Guanidine hydrochloride, 50 mM Tris pH 8.8 to place the fragment in solution.

The mixture was then adjusted to 10 mM DTT, incubated at 37° C. for 1 hour under $N_2$ and then adjusted to 50 mM iodoacetamide followed by an additional 1 hour at 37° C. DTT was again added to give a final concentration of 20 mM and the sample immediately dialyzed against Buffer C (25 mM Tris pH 8.0, 0.1 mM EDTA, 0.1 mM DTT, 20 mM KCl, 6M Urea).

The reduced and alkylated fragment was then subjected to Q-SEPHAROSE ion exchange chromatography. The sample was loaded on the column in Buffer C and then eluted with a gradient of 20–500 mM KCl in Buffer C. Reactions containing vWF fragment were pooled, dialyzed and concentrated via ultrafiltration.

The binding of vWF to glycoprotein Ib was measured in two experimental systems, in the presence of either ristocetin or botrocetin as modulators of binding. The inhibitory effect of the recombinant 52/48 kDa fragment was measured as a function of its concentration. In the assay, platelets were used at a final count of 1×10$^8$/ml, $^{125}$I-labeled vWF was at the concentration of 2 µg/ml, and ristocetin or botrocetin were used at 1.0 mg/ml or 0.4 µg/ml, respectively. The method for measuring vWF binding has been reported in detail in Ruggeri et al., *J. Clin. Invest.*, 72:1–12, 1983. The assays employing ristocetin or botrocetin are identical, except for the use of one modulator or the other.

Figure 10A:
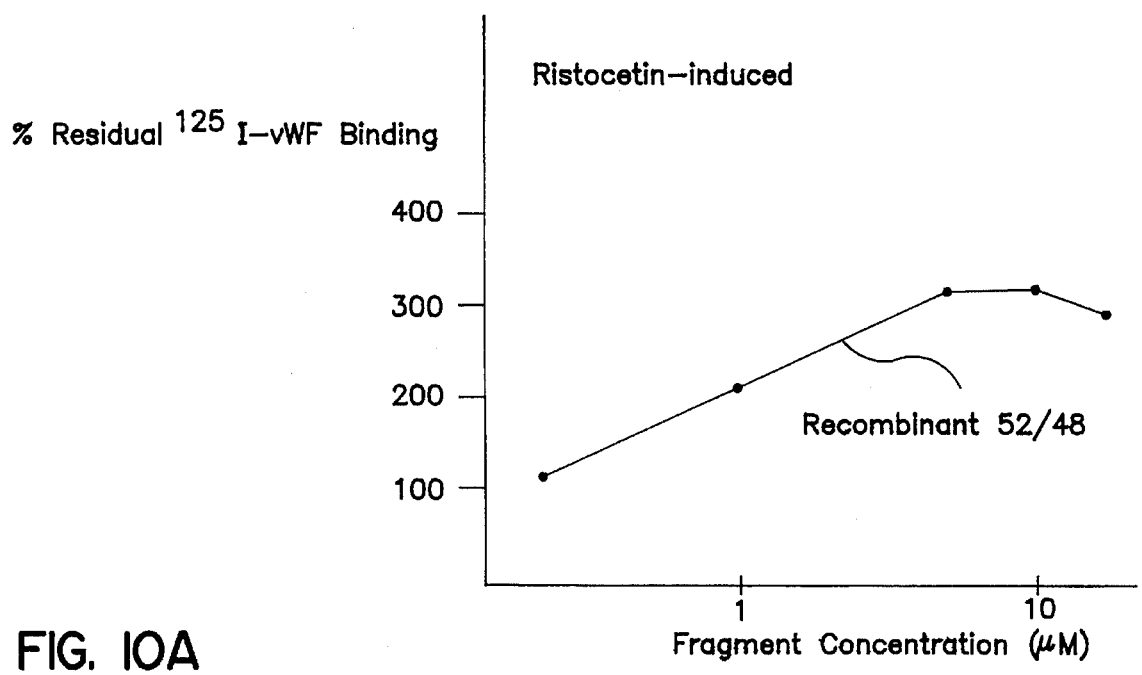
FIG. 10A illustrates the inhibiting activity of recombinantly produced vWF fragment in a ristocetin assay-system.
Figure 10B:
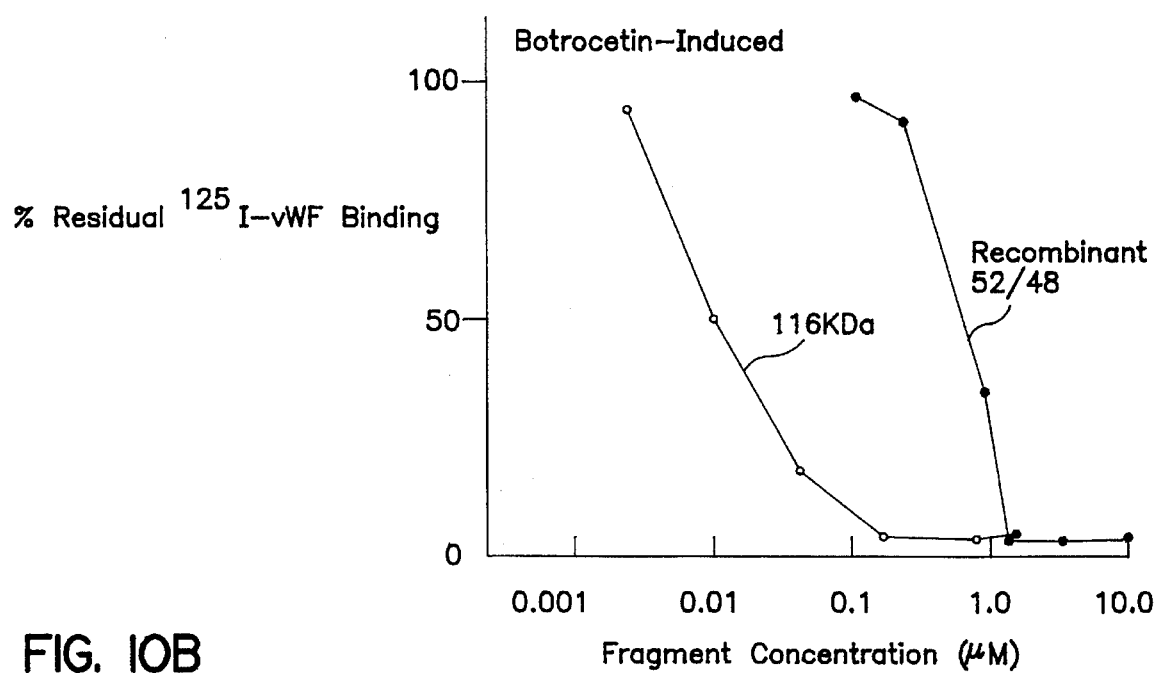
FIG. 10B illustrates the inhibiting activity of recombinantly produced vWF fragment in a botrocetin assay system.

The results of these studies are shown in FIG. 10. In the top panel (FIG. 10A) it can be seen that the recombinant 52/48 kDa fragment apparently fails to inhibit ristocetin-induced binding of vWF to glycoprotein Ib. The amount of vWF bound is actually increased paradoxically in the presence of the recombinant fragment. These results are the consequence of precipitation of the recombinant fragment in the presence of ristocetin. The molecular aggregates formed in these mixtures include radiolabeled vWF, so that radioactivity is precipitated with the platelets when these are separated from the soluble components of the assay mixture by centrifugation. The occurrence of precipitation was demonstrated in experiments where platelets were omitted from the incubation mixture, by showing that radioactivity was still precipitated by centrifugation. Thus, in this case, the presence of precipitated radioactivity is not expression of vWF binding to platelets, and the ristocetin-dependent assay is not a valid method to test the possible inhibitory effect of the recombinant 52/48 kDa fragment. Although ristocetin may be appropriate in evaluating apparent platelet aggregation (e.g. FIG. 8), a botrocetin-based assay is preferred for competition/inhibition studies.

The results presented in the bottom panel (FIG. 10B) clearly demonstrate that the recombinant vWF fragment inhibits binding of intact vWF to platelets in the presence of botrocetin. The dose-dependent inhibitory effect is compared to that of a proteolytic fragment of vWF, designated as 116 kDa, which is known to retain the native conformation of this domain of the molecule (Mohri et al., *J. Biol. Chem.*, 264:17361–17367, 1989). In this assay system, the recombinant 52/48 kDa fragment at a concentration of 2 µmol/L completely inhibits the binding of intact vWF to glycoprotein Ib.

Figure 11A:
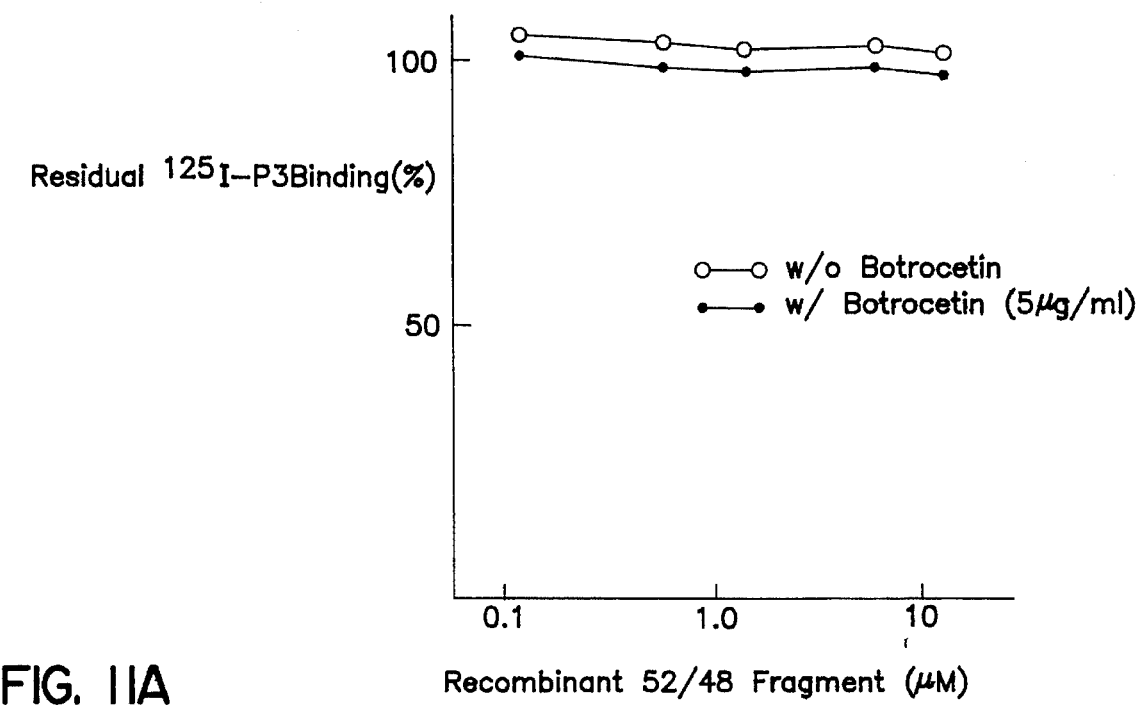
FIG. 11A illustrates the effect of the recombinantly produced vWF fragment on the binding of the noninhibitory anti-glycoprotein Ibα antibody (LJ-P3) to platelets in the presence and absence of botrocetin.
Figure 11B:
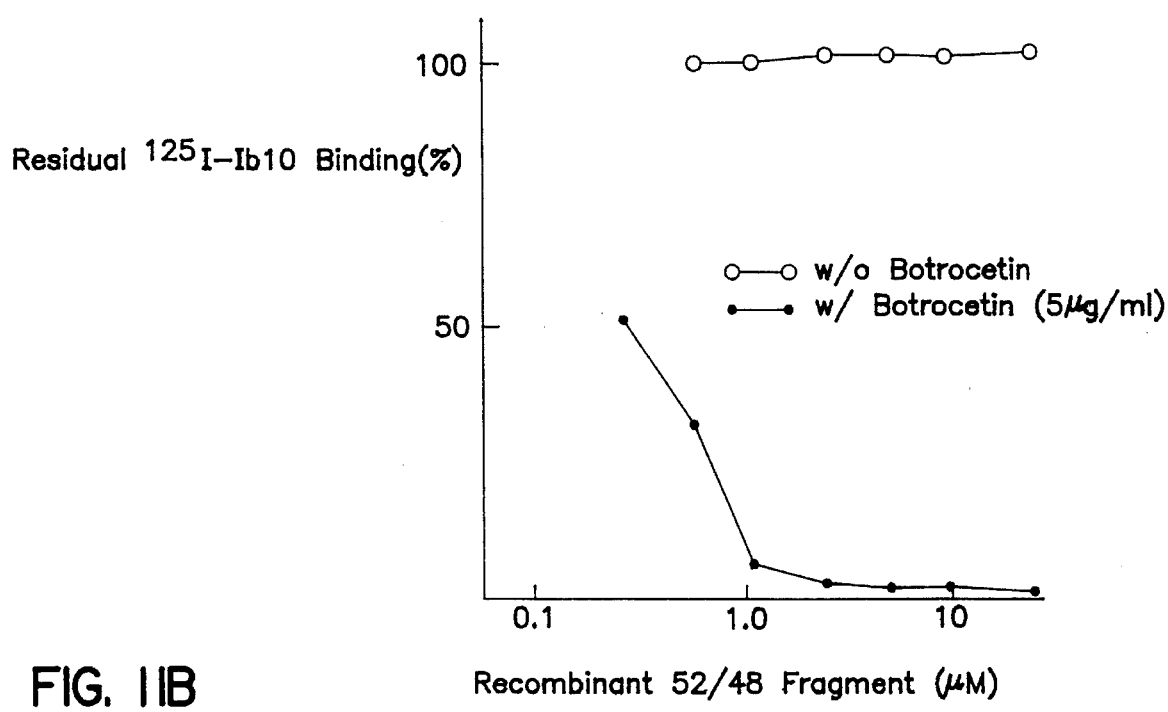
FIG. 11B illustrates the effect of the recombinantly produced vWF fragment on the binding of the inhibitory anti-glycoprotein Ibα antibody (LJ-Ib10) to platelets in the presence and absence of botrocetin.
Figure 12:
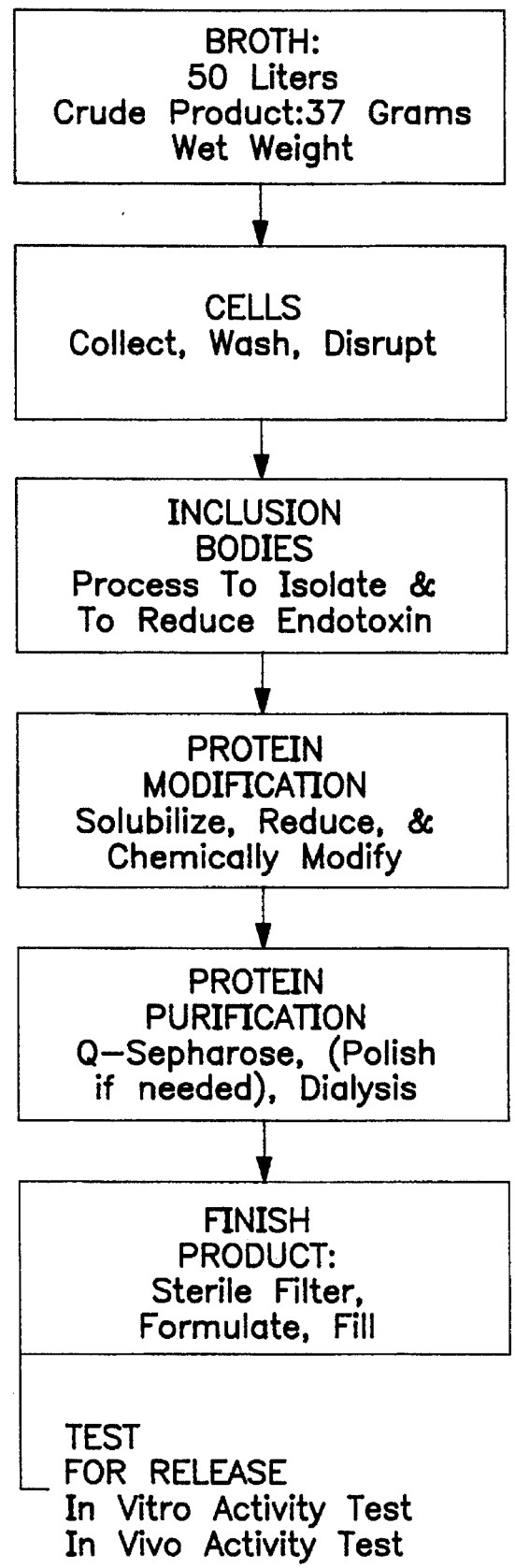
FIG. 12 illustrates diagramatically the operative steps in the purification process of the invention.
Figure 13:
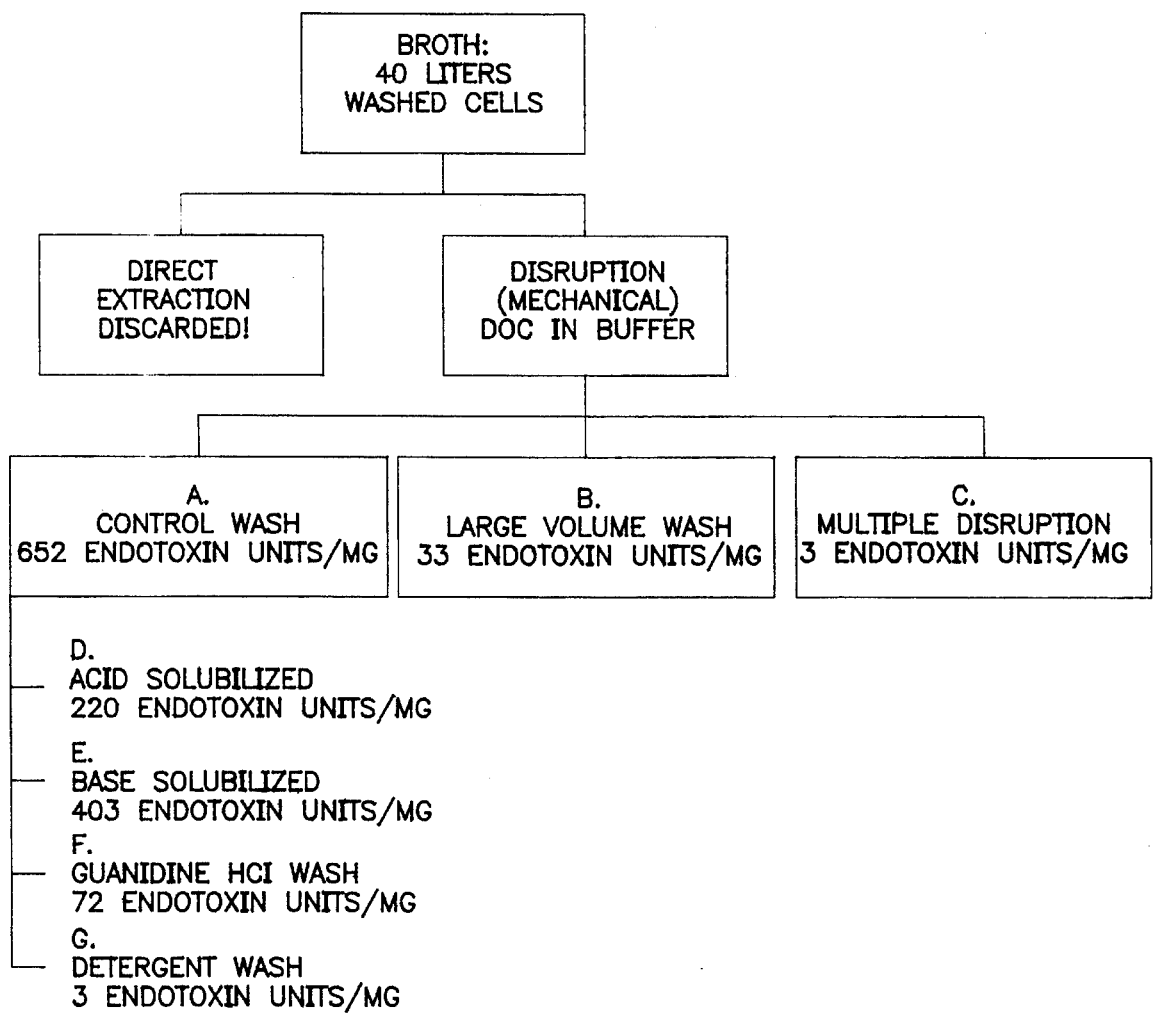
FIG. 13 illustrates diagramatically the matrix used to define conditions for endotoxin extraction from inclusion bodies.

Experiments were performed to demonstrate that the recombinant 52/48 kDa fragment of vWF binds to platelet glycoprotein Ib like the parent molecule. This demonstration proves that the inhibitory effect of the fragment on the platelet binding of the parent molecule is due to competitive occupancy of the platelet membrane receptor, and not to other unforeseen effects on the vWF molecule itself. One possible approach was to perform direct binding studies with the labeled recombinant fragment. However, labeling of the recombinant 52/48 kDa fragment with $^{125}$I, the standard approach for this kind of assays, resulted in an unstable molecule that could not be used in direct binding assays because of excessive nonspecific interactions. Therefore, these studies were based on the concept that binding of the recombinant molecule to the vWF-binding site of glycoprotein Ib should result in inhibition of binding of relevant monoclonal antibodies directed at epitopes overlapping with the functional site, but should have no effect on the binding of antibodies directed at other epitopes of glycoprotein Ib. Thus, two anti-glycoprotein Ibα antibodies, one inhibiting botrocetin-mediated vWF binding to platelets (LJ-Ib10) and the other with no inhibitory effect (LJ-P3), were labeled with $^{125}$I. The effect of the recombinant 52/48 kDa fragment on antibody binding to platelets was studied in the presence or absence of botrocetin, and the results are shown in FIG. 11. In the presence of botrocetin, the recombinant fragment inhibited binding of the inhibitory anti-glycoprotein Ib antibody to platelets (FIG. 11B), but not binding of the noninhibitory antibody (FIG. 11A). In the absence of botrocetin, the recombinant fragment had no effect on the binding of either antibody. Thus, in the presence of botrocetin, the recombinant fragment appears to bind to glycoprotein Ib at a site overlapping with the epitope of the inhibitory antibody LJ-Ib10, without interfering with the binding of the noninhibitory antibody LJ-P3. The inhibitory effect on vWF binding to glycoprotein Ib, therefore, appears to be related to the binding of the recombinant fragment to a specific functional site on glycoprotein Ibα.

Deposit of Strains Useful in Practicing the Invention

A deposit of biologically pure culture of the following strain was made with the American Type Culture Collection, 12301 Parklawn Drive, Rockville, Md., the accession number indicated was assigned after successful viability testing, and the requisite fees were paid. Access to said culture will be available during pendency of the patent application to one determined by the Commissioner to be entitled thereto under 37 C.F.R. §1.14 and 35 U.S.C. §122. All restriction on availability of said culture to the public will be irrevocably removed upon the granting of a patent based upon the application and said culture will remain permanently available for a term of at least five years after the most recent request for the furnishing of a sample and in any case for a period of at least 30 years after the date of the deposit. Should the culture become nonviable or be inadvertently destroyed, it will be replaced with a viable culture(s) of the same taxonomic description.

| Strain/Plasmid | ATCC No. | Deposit Date |
|---|---|---|
| BL21(DE3)pLysS/pET-8c52K(Km ®) | 68306 | April 17, 1990 |

EXAMPLE II

This Example illustrates the development of experimental conditions for practicing the invention. The studies were done for purposes of optimization not limitation of the invention.

A 40 liter batch of cells was washed in Tris-HCl buffered saline (0.25M Tris-HCl, 200 mM NaCl, pH 7.5). The 40 liters of cells were disrupted in Tris-CHl buffered saline to which sodium deoxycholate had been added (0.25M Tris-HCl, 200 mM NaCl, 0.5 g/l sodium deoxycholate, pH 7.5) by passage through the MICROFLUIDIZER. The disrupted cell suspension was immediately passed a second time through the MICROFLUIDIZER. The disrupted cell suspension was centrifuged to yield a pellet of crude inclusion bodies. The pellet of crude inclusion bodies was split into samples (A through G below) which were then subjected to further procedures to determine the best washing method, with one intent being to lower the residual endotoxin per milligram of product. The procedures and the results of endotoxin determinations are tabulated in Table 1. It should be noted that because of the nature of inclusion bodies, the endotoxin measurements were carried out after each experimental batch had been reduced, carboxymethylated, and subjected to chromatography.

Condition A, the Control Wash, is described below and yielded the material to which all other materials were compared. A portion of the inclusion body pellet was processed by resuspension in buffer I (0.05M Tris, 0.002 M disodium EDTA, 0.002M dithiothreitol, pH 9, 5% (v/v) glycerol) at a ratio of 35 ml of buffer I per gram wet weight of pellet. The suspension was centrifuged to yield a pellet. The pellet was resuspended in buffer II, which is comprised of buffer I to which was added 0.5 g/liter sodium deoxycholate, and collected by centrifugation. The pellet was recovered and resuspended in buffer II, and centrifuged. The pellet was recovered, resuspended in buffer I (no sodium deoxycholate present), and centrifuged. The recovered pellet was labeled as control material, or sample A in the protocol.

By comparison, the "Large Volume Wash", or B, was resuspended in 70 ml per gram wet weight material, and an extra step was inserted in the scheme. The extra step was to resuspend in Buffer II with subsequent passage through the MICROFLUIDIZER. Then the standard last step was carried out: centrifugation, wash in buffer I, and centrifugation to collect the final pellet which was coded and passed on for analysis.

"Multiple Disruption", or C in the flow chart, was similar to the Control A above, except that every wash included passage through the MICROFLUIDIZER.

"Acid solubilized", or D in the flow chart, designates material which was resuspended in 1N acetic acid, 0.5M urea, for two wash cycles, and otherwise treated as in Control A.

"Base solubilized", or E in the flow chart, refers to material which was washed once in 0.01N NaOH, and otherwise treated as in Control A.

"Guanidine HCl Wash", or F in the flow chart, refers to material which was washed once in buffer I which in addition contained 0.5M guanidine HCl. The sample was otherwise treated as in Control A.

"Detergent Wash", or G in the flow chart, refers to material which was washed twice in 0.1% Tween 20 once, and otherwise treated as in Control A.

As the table indicates, the control batch, A, was measured as having 652 endotoxin units/mg protein. The residual endotoxin was considerably reduced by increasing the volume of the wash, in B, but this step also included one passage through the disrupter. The multiple disruption experiment, condition C, was designated as one of the conditions which should be incorporated into the process improvement. Likewise, the detergent wash, or condition G, was also chosen as useful, and incorporated into the process improvement.

TABLE 1

| | Description | Endotoxin Units/mg protein |
|---|---|---|
| A | Control Wash | 652 EU/mg |
| B | Large Volume & extra disruption | 33 EU/mg |
| C | Multiple disruption | 3 EU/mg |
| D | Acid wash | 220 EU/mg |
| E | Base Wash | 403 EU/mg |
| F | Guanidine HCl wash | 72 EU/mg |
| G | Detergent (Tween 20) wash | 3 EU/mg |

What is claimed is:

1. A process for removing endotoxins and DNA from inclusion bodies containing the 52/48 kDa tryptic fragment of vWF or peptide subfragments thereof, comprising:

mechanically disrupting said inclusion bodies in an aqueous buffer comprising at least one detergent;

forming a washed pellet from said mechanically disrupted inclusion bodies;

dissolving the washed pellet in a denaturant to form a suspension containing the 52/48 kDa tryptic fragment of vWF or peptide subfragments thereof;

alkylating the 52/48 kDa tryptic fragment of vWF or peptide subfragments thereof;

subjecting the alkylated 52/48 kDa tryptic fragment of vWF or peptide subfragments thereof to column chromatography; and recovering the alkylated 52/48 kDa tryptic fragment of vWF or peptide subfragments thereof from the column by elution.

2. A process according to claim 1 wherein said buffer comprises at least two detergents.

3. A process according to claim 1 wherein said mechanical disruption and said washed pellet formation is repeated from about three to about ten times.

4. The process according to claim 1 wherein the detergents are selected from the group consisting of bile salts, ionic detergents and non-ionic surfactants.

5. The process according to claim 4 wherein the detergents are selected from the group consisting of cholate, deoxycholate, lithocholate, anionic-, cationic-, and zwitterionic- detergents, polyoxyethylene sorbitol esters, and polyoxyethylene p-t octylphenol.

6. The process according to claim 5 wherein the detergents are selected from deoxycholate and TWEEN-80.

7. The process according to claim 1 wherein the denaturant is selected from the group consisting of Guanidine hydrochloride, Guanidine thiocyanate and urea.

8. The process according to claim 7 wherein the denaturant is Guanidine hydrochloride and is present at a concentration of about 2.5M to about 8M.

9. The process according to claim 8 wherein the Guanidine hydrochloride is present at a concentration of about 6M.

10. The process according to claim 1 wherein said denaturant optionally contains a salt.

11. The process according to claim 1 wherein said alkylation is conducted in the presence of a sulfhydryl reducing agent and an alkylating agent in a nitrogen atmosphere.

12. The process according to claim 11 wherein said sulfhydryl reducing agent is dithiothreitol and said alkylating agent is iodoacetamide.

13. The process according to claim 1 wherein said column comprises Q-SEPHAROSE.

14. The process according to claim 1 wherein said elution is by means of a salt gradient.

15. The process according to claim 14 wherein said gradient ranges from about 20–500 mM KCl.

16. A process for recovery of the 52/48 kDa tryptic fragment of vWF or peptide subfragments thereof produced in the form of inclusion bodies from recombinant host cells containing the same, comprising the steps of:

(a) providing a washed recombinant host cell suspension;

(b) subjecting the cell suspension to a first mechanical disruption;

(c) adding one or more detergents;

(d) subjecting the suspension subjected to Said first mechanical disruption to a second mechanical disruption;

(e) centrifuging the suspension subjected to said second mechanical disruption to provide a pellet containing inclusion bodies;

(f) resuspending the pellet containing inclusion bodies in a buffer comprising said one or more detergents;

(g) subjecting the resuspended pellet to a third mechanical disruption;

(h) washing the resuspended pellet containing inclusion bodies, which has been subjected to said third mechanical disruption by repeated cycles of centrifugation and resuspension in a buffer; and (i) recovering the inclusion bodies.

17. The process according to claim 1, wherein the washed recombinant host cell suspension of step (a) has a concentration of about 0.01 gm wet wt/ml to about 0.5 gm wet wt/ml.

18. The process according to claim 16 wherein said detergents are selected from the group consisting of bile salts, anionic detergents, cationic detergents, zwitterionic detergents and non-ionic surfactants.

19. The process according to claim 16 wherein said detergents are selected from the group consisting of cholate, deoxycholate, lithocholate, anionic-, cationic-, and zwitterionic detergents, polyoxyethylene sorbitol esters and polyoxyethylene p-t octylphenol.

20. The process according to claim 19 wherein the detergents are selected from deoxycholate and Tween-80.

21. The process according to claim 20 wherein said deoxycholate is present in a concentration of from about 0.001 g/l to about 50 g/l.

22. The process according to claim 21 wherein the concentration of deoxycholate is about 0.5 g/liter.

23. The process according to claim 20 wherein said Tween 80 is present at a concentration of about 0.0001% to about 50% (v/v).

24. The process according to claim 23 wherein the concentration of Tween 80 is about 0.025% (v/v).

25. The process according to claim 16 wherein step (h) is repeated at least three times.

26. The process according to claim 16 wherein step (h) is repeated at least six times.

27. The process according to claim 16 wherein the final cycle of washing is conducted in the absence of detergent.

28. A process for recovery of the 52/48 kDa tryptic fragment of vWF or peptide subfragments thereof produced in the form of inclusion bodies from recombinant host cells containing the same, comprising the steps of:

(a) providing a washed recombinant host cell suspension;

(b) adding a first detergent;

(c) subjecting the cell suspension to a first mechanical disruption;

(d) adding a second detergent;

(e) subjecting the suspension subjected to said first mechanical disruption to a second mechanical disruption;

(f) centrifuging the suspension subjected to said second mechanical disruption to provide a pellet containing inclusion bodies;

(g) resuspending the pellet containing inclusion bodies in a buffer comprising said first and second detergents;

(h) subjecting the resuspended pellet containing inclusion bodies to a third mechanical disruption;

(i) washing the resuspended pellet containing inclusion bodies, which has been subjected to said third mechanical disruption by repeated cycles of centrifugation and resuspension in a buffer; and (j) recovering the inclusion bodies.

29. The process according to claim 28 wherein the washed recombinant host cell suspension of step (a) has a concentration of about 0.01 gm wet wt/ml to about 0.5 gm wet wt/ml.

30. The process according to claim 28 wherein said first detergent is selected from the group consisting of bile salts, anionic detergents, cationic detergents and zwitterionic detergents.

31. The process according to claim 30 wherein said first detergent is deoxycholate.

32. The process according to claim 31 wherein said deoxycholate is present in a concentration of from about 0.0001 g/l to about 50 g/l.

33. The process according to claim 32 wherein the concentration of deoxycholate is about 0.5 g/liter.

34. The process according to claim 28 wherein said second detergent is selected from the group consisting of Tween 80, Tween 20, Triton N-101, Triton X-100 and Triton NP-40.

35. The process according to claim 34 wherein said second detergent is Tween 80.

36. The process according to claim 35 wherein said Tween 80 is present at a concentration of about 0.0001% to about 50% (v/v).

37. The process according to claim 36 wherein the concentration of Tween 80 is about 0.025% (v/v).

38. The process according to claim 28 wherein the inclusion bodies are recovered after at least 3 cycles of washing, wherein the first two cycles are conducted in a buffer comprising said first and second detergent and the third cycle is conducted in a buffer in the absence of both detergents.

39. A process according to claim 28, wherein step (j) comprises:
   (1) dissolving the washed inclusion bodies in a denaturant to form a suspension containing the 52/48 kDa tryptic fragment of vWF or peptide subfragments thereof;
   (2) alkylating the 52/48 kDa tryptic fragment of vWF or peptide subfragments thereof;
   (3) subjecting the alkylated 52/48 kDa tryptic fragment of vWF or peptide subfragments thereof to column chromatography; and
   (4) recovering the alkylated 52/48 kDa tryptic fragment of vWF or peptide subfragments thereof from the column by elution.

40. The process according to claim 39 wherein the denaturant is selected from the group consisting of Guanidine hydrochloride, Guanidine thiocyanate and urea.

41. The process according to claim 40 wherein the denaturant is Guanidine hydrochloride and is present at a concentration of about 2.5M to about 8M.

42. The process according to claim 41 wherein the Guanidine hydrochloride is present at a concentration of about 6M.

43. The process according to claim 39 wherein said alkylation is conducted in the presence of a sulfhydryl reducing agent and an alkylating agent in a nitrogen atmosphere.

44. The process according to claim 43 wherein said sulfhydryl reducing agent is dithiothreitol and said alkylating agent is iodoacetamide.

45. The process according to claim 39 wherein said column comprises Q-SEPHAROSE.

46. The process according to claim 39 wherein said elution is by means of a salt gradient.

47. The process according to claim 46 wherein said gradient ranges from about 20–500 mM KCl.

* * * * *